(12) United States Patent
Back et al.

(10) Patent No.: US 11,186,538 B2
(45) Date of Patent: Nov. 30, 2021

(54) TWIN TAIL AMINE COMPOUNDS AND THEIR ZWITTERIONIC DERIVATIVES

(71) Applicant: RHODIA OPERATIONS, Paris (FR)

(72) Inventors: Olivier Back, Lyons (FR); Roberto Company, Bordeaux (FR); Hong Liu, Pennington, NJ (US); Rémy Leroy, Mions (FR); Philippe Marion, Vernaison (FR)

(73) Assignee: RHODIA OPERATIONS, Paris (FR)

( * ) Notice: Subject to any disclaimer, the term of this patent is extended or adjusted under 35 U.S.C. 154(b) by 13 days.

(21) Appl. No.: 16/347,994

(22) PCT Filed: Nov. 8, 2017

(86) PCT No.: PCT/EP2017/078672
§ 371 (c)(1),
(2) Date: May 7, 2019

(87) PCT Pub. No.: WO2018/087188
PCT Pub. Date: May 17, 2018

(65) Prior Publication Data
US 2019/0292129 A1    Sep. 26, 2019

(30) Foreign Application Priority Data

Nov. 8, 2016 (EP) .................................... 16306467
Nov. 8, 2016 (EP) .................................... 16306469
(Continued)

(51) Int. Cl.
*A01N 25/30* (2006.01)
*C07C 291/04* (2006.01)
(Continued)

(52) U.S. Cl.
CPC ............ *C07C 211/14* (2013.01); *A01N 25/30* (2013.01); *C07C 209/78* (2013.01);
(Continued)

(58) Field of Classification Search
CPC ... C07C 211/14; C07C 291/04; C07C 211/63; C07C 209/78
See application file for complete search history.

(56) References Cited

U.S. PATENT DOCUMENTS

| | | | |
|---|---|---|---|
| 4,415,487 A | 11/1983 | Blaschke et al. | |
| 4,879,859 A | 11/1989 | Dykmans | |

(Continued)

FOREIGN PATENT DOCUMENTS

| | | | |
|---|---|---|---|
| WO | 2001095720 A1 | 12/2001 | |
| WO | 2012150343 A1 | 11/2012 | |

(Continued)

OTHER PUBLICATIONS

Wikipedia, Wikipedia, Aliphatic Compound, 2020, pp. 1-3, recovered from https://en.wikipedia.org/wiki/Aliphatic_compound on Aug. 24, 2020. (Year: 2020).*

(Continued)

*Primary Examiner* — Amy C Bonaparte
(74) *Attorney, Agent, or Firm* — Osha Bergman Watanabe & Burton LLP

(57) ABSTRACT

A compound of general formula (I) or (II), wherein $R_n$ and $R_m$ independently represent a $C_3$-$C_{27}$ aliphatic group, $R_1$ to $R_4$, which may be the same or different at each occurrence, represent hydrogen or a $C_1$-$C_8$ alkyl group, $X_1$ and $X_2$, which may be the same or different at each occurrence, represent a linear or branched divalent hydrocarbon radical with 1 to 24 carbon atoms which can be optionally substituted and/or interrupted by one or more heteroatoms or
(Continued)

heteroatom containing groups, and $R_5$ and $R_6$, which may be the same or different at each occurrence, represent a group selected from —O⁻, -Alk-CH(OH)—CH$_2$—SO$_3$— and -Alk-CO$_2$— wherein Alk represents an alkylene group.

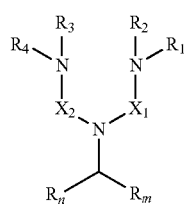

(I)

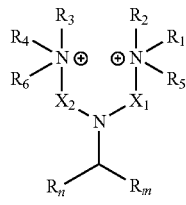

(II)

14 Claims, 3 Drawing Sheets

(30) Foreign Application Priority Data

Nov. 8, 2016 (EP) ..................................... 16306470
Aug. 17, 2017 (WO) ................. PCT/EP2017/070884
Oct. 31, 2017 (EP) ..................................... 17306496

(51) Int. Cl.
| | | |
|---|---|---|
| *C07C 229/12* | (2006.01) |
| *C07C 309/14* | (2006.01) |
| *C07C 211/14* | (2006.01) |
| *C07C 209/78* | (2006.01) |
| *C07C 211/63* | (2006.01) |

(52) U.S. Cl.
CPC .......... *C07C 211/63* (2013.01); *C07C 229/12* (2013.01); *C07C 291/04* (2013.01); *C07C 309/14* (2013.01)

(56) References Cited

U.S. PATENT DOCUMENTS

| 5,747,471 A | 5/1998 | Siegel et al. |
| 2014/0371293 A1 | 12/2014 | Brown et al. |
| 2015/0374842 A1* | 12/2015 | Brown ................... A61K 47/60 536/24.5 |

FOREIGN PATENT DOCUMENTS

| WO | 2018033607 A1 | 2/2018 |
| WO | 2018087179 A1 | 5/2018 |
| WO | 2018087181 A1 | 5/2018 |

OTHER PUBLICATIONS

Zaragoza Dorwald, Side Reactions in Organic Synthesis, 2005, WILEY-VCH Verlag GmbH & Co. KGaA, Weinheim, Preface. p. IX. (Year: 2005).*

* cited by examiner

TWIN TAIL AMINE COMPOUNDS AND THEIR ZWITTERIONIC DERIVATIVES

CROSS-REFERENCE TO RELATED APPLICATIONS

This application is a U.S. national stage entry under 35 U.S.C. 071 of International Application No. PCT/EP2017/078672 filed Nov. 8, 2017, which claims priority to European application No. 16306467.8, filed on Nov. 8, 2016, European application No. 16306469.4, filed on Nov. 8, 2016, European application No. 16306470.2, filed on Nov. 8, 2016, International application No. PCT/EP2017/070884, filed on Aug. 17, 2017, and European application No. 17306496.5, filed on Oct. 31, 2017. The entire contents of these applications are explicitly incorporated herein by this reference.

The present invention relates to new twin tail amine compounds and their zwitterionic derivatives and processes for their preparation.

Amine compounds and zwitterionic derivatives thereof are used in various applications as surfactants.

BACKGROUND OF THE TECHNOLOGY

Surfactants are compounds that lower the surface tension (or interfacial tension) between two liquids, a liquid and a gas or between a liquid and a solid. Surfactants may act as detergents, wetting agents, emulsifiers, foaming agents, and dispersants.

Surfactants are usually organic compounds that are amphiphilic, meaning they contain both hydrophobic groups (their tails) and hydrophilic groups (their heads). Therefore, a surfactant contains both a water-insoluble (or oil-soluble) component and a water-soluble component. Surfactants will diffuse in water and adsorb at interfaces between air and water or at the interface between oil and water, in the case where water is mixed with oil. The water-insoluble hydrophobic group may extend out of the bulk water phase, into the air or into the oil phase, while the water-soluble head group remains in the water phase.

Surfactants are routinely deposited in numerous ways on land and into water systems, whether as part of an intended process or as industrial and household waste. Some of them are known to be toxic to animals, ecosystems, and humans, and can increase the diffusion of other environmental contaminants.

WO 2012/150343 relates to agrochemical compositions comprising a tertiary amide of formula (I) or (II)

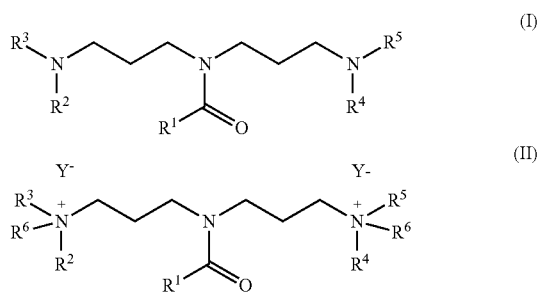

wherein $R^1$ is an aliphatic group having 5-23 carbon atoms, $R^2$, $R^3$, $R^4$ and $R^5$ are independently hydrogen, $-CH_2CH_2OH$, $CH_2-CH(CH_3)OH$ or an aliphatic group with 1 to 5 carbon atoms, $R^6$ is hydrogen or an aromatic group having 1-22 carbon atoms and $Y^-$ is an anion.

EP 1 289 362 describes the use of amine compounds with improved biodegradability as adjuvants. The compounds are based on dialkylamino propylamine, wherein the alkyl groups are $C_1$ to $C_5$ alkyl chains which are converted into an amidoamine by reaction with a $C_8$ to $C_{22}$ fatty acid.

The foregoing amine and amide compounds have interesting properties as surfactants, but there is still a need for improvement of surfactants in terms of biodegradability and toxicity. There is also a need to develop surfactants that are obtainable from readily available starting materials, preferably from starting materials derived from renewable resources.

It was thus an object of the present invention to provide new compounds which may i.a. be used as surfactants and which show an improved combination of biodegradability, toxicity and which advantageously are available from renewable or natural resources.

This object has been achieved with the compounds of formula (I) or (II) in accordance with claim 1.

Preferred embodiments of the compounds in accordance with the present invention are set forth in the dependent claims and in the detailed specification hereinafter.

A further embodiment of the present invention relates to processes for the manufacture of the compounds in accordance with the present invention.

DETAILED DESCRIPTION OF THE INVENTION

Figure 1:
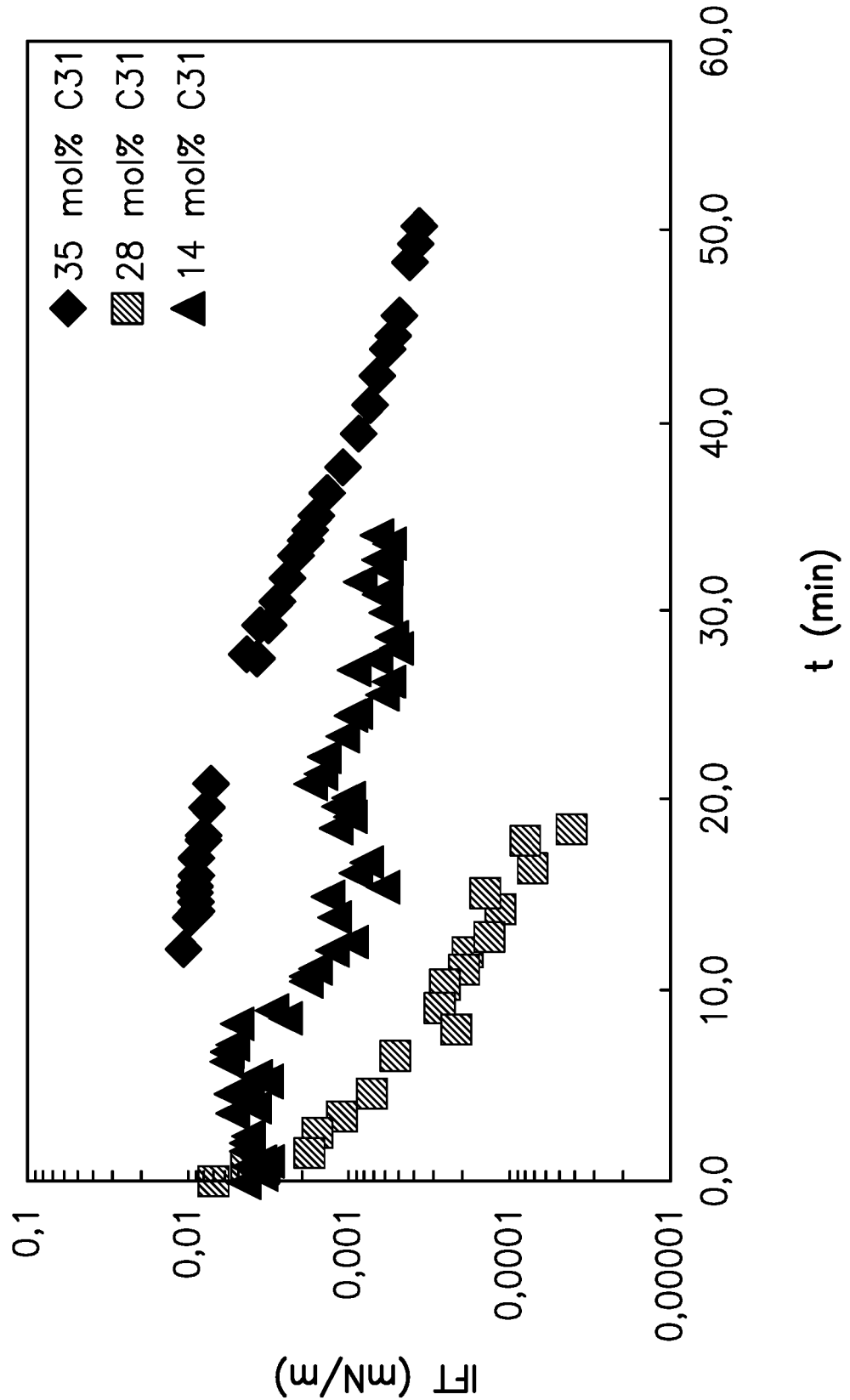
FIG. 1 shows the interfacial tension (IFT) behaviour between oil and brine of a mixture of compounds of formula (II) in accordance with the present invention for a crude oil with a total acid number (TAN) of 2. TAN is defined as the amount of KOH in miligrams that is needed to neutralize the acids in one gram of oil.

The compounds according to the present invention are represented by formula (I) or formula (II)

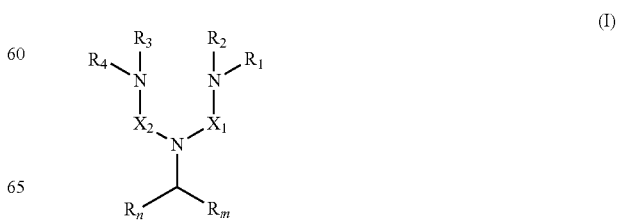

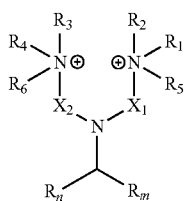

(II)

wherein $R_n$ and $R_m$ independently represent a $C_3$-$C_{27}$ aliphatic group, $R_1$ to $R_4$, which may be the same or different at each occurrence, represent hydrogen or a $C_1$-$C_8$ alkyl group, $X_1$ and $X_2$, which may be the same or different at each occurrence, represent a linear or branched divalent hydrocarbon radical with 1 to 24 carbon atoms which can be optionally substituted and/or interrupted by one or more heteroatoms or heteroatom containing groups, and $R_5$ and $R_6$, which may be the same or different at each occurrence, represent a group selected from —O⁻, -Alk-CH(OH)—CH$_2$—SO$_3$— and -Alk-CO$_2$ wherein Alk represents an alkylene group.

$R_n$ and $R_m$ represent a $C_3$-$C_{27}$ aliphatic group, very often a $C_3$-$C_{19}$ aliphatic group, often a aliphatic $C_7$-$C_{17}$ group.

The number of carbon atoms of $R_n$ and $R_m$ can be even or odd numbers. $R_n$ and $R_m$ may be identical to each other or, alternatively, $R_n$ and $R_m$ may differ from each other.

The number of carbon atoms of $R_n$ and of $R_m$, as herein represented by the couple (n,m), can be notably any of the following couples:

(3,3), (5,5), (7,7), (9,9), (11,11), (13,13), (15,15), (17,17), (19,19), (21,21), (23,23), (25,25), (27,27)

(7,9), (7,11), (7,13), (7,15), (7,17), (7,19), (7,21), (7,23), (7,25), (7,27)

(9,11), (9,13), (9,15), (9,17), (9,19), (9,21), (9,23), (9,25), (9,27)

(11,13), (11,15), (11,17), (11,19), (11,21), (11,23), (11,25), (11,27)

(13,15), (13,17), (13,19), (13,21), (13,23), (13,25), (13,27)

(15,17), (15,19), (15,21), (15,23), (15,25), (15,27)

(17,19), (17,21), (17,23), (17,25), (17,27)

(19,21), (19,23), (19,25), (19,27)

(21,23), (21,25), (21,27)

(23,25), (23,27) or (25,27).

The aliphatic groups $R_n$ and $R_m$ may be linear or branched.

The aliphatic groups $R_n$ and $R_m$ may be free of any double bond and of any triple bond. Alternatively, the aliphatic groups $R_n$ and $R_m$ may comprise at least one —C═C— double bond and/or at least one —C≡O— triple bond.

The aliphatic groups $R_n$ and $R_m$ are advantageously chosen from alkyl groups, alkenyl groups, alkanedienyl groups, alkanetrienyl groups and alkylnyl groups.

Preferably, the aliphatic groups $R_n$ and $R_m$ are independently chosen from alkyl and alkenyl groups.

More preferably, the aliphatic groups $R_n$ and $R_m$ are independently chosen from alkyl and alkenyl groups, generally from $C_3$-$C_{27}$ alkyl and $C_3$-$C_{27}$ alkenyl groups, very often from $C_3$-$C_{19}$ alkyl and $C_3$-$C_{19}$ alkenyl groups and often from (i) $C_6$-$C_{17}$ alkyl and $C_6$-$C_{17}$ alkenyl groups or from (ii) $C_7$-$C_{17}$ alkyl and $C_7$-$C_{17}$ alkenyl groups. More preferably, $R_n$ and $R_m$ independently represent an alkyl group, generally a $C_3$-$C_{27}$ alkyl group, very often a $C_3$-$C_{19}$ alkyl group, often a $C_6$-$C_{17}$ alkyl group or a $C_7$-$C_{17}$ alkyl group.

$R_1$ to $R_4$, which may be the same or different at each occurrence in the compounds in accordance with the present invention, represent hydrogen or a $C_1$-$C_8$ alkyl group, preferably an alkyl group having from 1 to 6 carbon atoms and in particular may be methyl, ethyl, propyl, isopropyl, n-butyl, iso-butyl, or tert-butyl. In accordance with a particularly preferred embodiment $R_1$ to $R_4$ are methyl. If $R_1$ to $R_4$ are alkyl groups, they may be linear or branched.

$R_5$ and $R_6$, which may be the same or different at each occurrence, represent a group selected from —O⁻, -Alk-CH(OH)—CH$_2$—SO$_3$— and -Alk-CO$_2$— wherein Alk represents a divalent alkylene group, which may be linear or branched. Alk represents preferably a $C_1$-$C_{20}$ alkylene group, preferably a $C_1$-$C_{12}$ alkylene group, more preferably a $C_1$-$C_8$ alkylene group. In accordance with particularly preferred embodiments Alk is —CH$_2$—, —CH$_2$—CH$_2$—, —CH$_2$—CH$_2$—CH$_2$—, —CH$_2$—CH(CH$_3$)—, —CH$_2$—CH(CH$_3$)—CH$_2$— and the most preferred Alk is a methylene group —CH$_2$—.

A first group of preferred compounds in accordance with the present invention are compounds of formula (I) wherein $X_1$ and $X_2$ are (—CH$_2$-)$_m$ with m being an integer equal to 2 or from 3 to 20 and $R_1$ to $R_4$ are hydrogen or an alkyl group with 1 to 6 carbon atoms.

Another group of preferred compounds in accordance with the present invention are compounds of formula (I) wherein $X_1$ and $X_2$ are —(CH$_2$)$_3$— and $R_1$ to $R_4$ are methyl.

Still another group of preferred compounds in accordance with the present invention are compounds of formula (I) wherein $X_1$ and $X_2$ are a branched divalent hydrocarbon group, which may be optionally substituted and/or interrupted by one or more heteroatoms or heteroatom containing groups and $R_1$ to $R_4$ are as defined in claim 1.

Yet another group of preferred compounds in accordance with the present invention are compounds of formula (I) wherein $X_1$ and $X_2$ are a linear or branched divalent hydrocarbon group substituted and/or interrupted by one or more heteroatoms or heteroatom containing groups and $R_1$ to $R_4$ are as defined in claim 1.

A first group of compounds of formula (II) in accordance with the present invention are compounds wherein $X_1$ and $X_2$ are —(CH$_2$)$_3$—, $R_1$ to $R_4$ are methyl and $R_5$ and $R_6$ are —CH$_2$—CH(OH)—CH$_2$—SO$_3$ or —CH$_2$—CO$_2$—.

Another group of preferred compounds in accordance with the present invention are compounds of formula (II) wherein $X_1$ and $X_2$ are —(CH$_2$)$_3$—, $R_1$ to $R_4$ are methyl and $R_5$ and $R_6$ are —O⁻.

Still another group of preferred compounds in accordance with the present invention are compounds of formula (II) wherein $X_1$ and $X_2$ are a branched divalent hydrocarbon group, which may be optionally substituted and/or interrupted by one or more heteroatoms or heteroatom containing groups and $R_1$ to $R_6$ are as defined in claim 1.

Still another group of preferred compounds in accordance with the present invention are compounds of formula (II) wherein $X_1$ and $X_2$ are an aliphatic divalent group containing 2 to 20 carbon atoms with the exception of —(CH$_2$)$_3$— and $R_1$ to $R_6$ are as defined in claim 1.

Still another group of preferred compounds in accordance with the present invention are compounds of formula (II) wherein $X_1$, $X_2$, $R_n$, $R_m$, $R_5$ and $R_6$ are as defined in claim 1 and $R_1$ to $R_4$ are a $C_2$-$C_8$ alkyl group.

Compounds (I) and (II) wherein $R_m$ and $R_n$ differ from each other can be obtained from a mixture of fatty acids having different chain lengths. For example, using a mixture of two fatty acids $R_m$—COOH and $R_n$—COOH with m≠n, a mixture comprising a first compound (I) or (II) with aliphatic groups ($R_m$, $R_m$), a second compound with aliphatic groups ($R_m$, $R_n$) and a third compound with aliphatic groups ($R_n$, $R_n$) is generally obtained, and the compounds of the so-obtained mixture can then be optionally separated using common separation techniques that are well known to the skilled person. More generally, when using N fatty acids having different chain lengths, wherein N is an integer greater than or equal to 2, a mixture comprising (N+$C_N^2$) compounds of formula (I) or (II) is generally obtained, wherein $$C_N^2 = \tfrac{1}{2} \cdot N!/(N-2)!$$

Hence, an aspect of the present invention relates to a mixture comprising (N+$C_N^2$) compounds of formula (I) wherein N is an integer greater than or equal to 2 (for example, N can be from 2 to 20). Another aspect of the present invention relates to a mixture comprising (N+$C_N^2$) compounds of formula (II) wherein N is an integer greater than or equal to 2 (for example, N can be from 2 to 20).

In accordance with a first process in accordance with the present invention, the compounds of formula (I) are obtained by a process wherein an internal ketone K1 of formula (III), which can notably be obtained by a process P of decarboxylative ketonization, is reacted with a twin-tail amine of formula (IV), which is a triamine, under reductive amination conditions in accordance with the following general reaction scheme

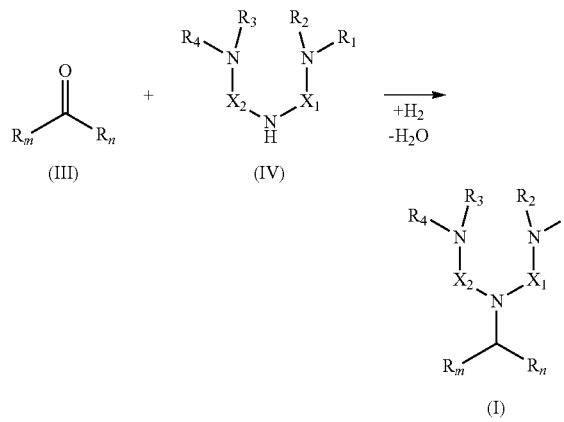

wherein $R_n$, $R_m$, $X_1$, $X_2$ and $R_1$ to $R_4$ in the above scheme have the meanings as defined above for the compounds in accordance with the present invention.

This amination reaction is preferably performed by reacting the ketone (III) and the amine (IV) in the presence of a transition metal (e.g. Ni, Co, Cu, Fe, Rh, Ru, Ir, Pd, Pt) based catalyst (typically Pd/C), in a autoclave under hydrogen pressure (typically from 1 atm to 200 bar).

An internal ketone is generally a compound of formula (III)

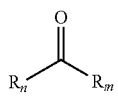

(III)

wherein $R_n$ and $R_m$ independently represent an aliphatic group, generally a $C_3$-$C_{27}$ aliphatic group, very often a $C_3$-$C_{19}$ aliphatic group, often an aliphatic $C_6$-$C_{17}$ group or $C_7$-$C_{17}$ group.

Preferably, the aliphatic groups $R_n$ and $R_m$ are independently chosen from alkyl and alkenyl groups, generally from $C_3$-$C_{27}$ alkyl and $C_3$-$C_{27}$ alkenyl groups, very often from $C_3$-$C_{19}$ alkyl and $C_3$-$C_{19}$ alkenyl groups and often either from $C_6$-$C_{17}$ alkyl and $C_6$-$C_{17}$ alkenyl groups or from $C_7$-$C_{17}$ alkyl and $C_7$-$C_{17}$ alkenyl groups. More preferably, $R_n$ and $R_m$ independently represent an alkyl group, generally a $C_3$-$C_{27}$ alkyl group, very often a $C_3$-$C_{19}$ alkyl group, often a $C_6$-$C_{17}$ group or a $C_7$-$C_{17}$ alkyl group.

According to a possible embodiment, the reaction is carried out in a solvent. However, the presence of such a solvent is not compulsory and according to a specific embodiment, no solvent is used for this step. The exact nature of the solvent, if any, may be determined by the skilled person. Typical suitable solvents include, without limitation, methanol, ethanol, isopropanol, tert-butanol, THF, 2-methyltetrahydrofuran, 1,4-dioxane, dimethoxyethane, diglyme and mixtures thereof.

Besides, the amination is usually carried out at a temperature ranging from 15° C. to 400° C. and may be conducted batchwise, semi-continuously or continuously and generally performed either in a batch mode or in a continuous mode using a fixed-bed catalyst (gas-solid or gas-liquid-solid process).

Preferred amines of formula (IV) are amines where $X_1$ and $X_2$ are —$CH_2$—$CH_2$— or —$(CH_2)_m$— wherein m is an integer from 3 to 20 and $R_1$ to $R_4$ independently represent hydrogen or an alkyl group having 1 to 6 carbon atoms (such as e.g. —$CH_3$, —$CH_2CH_3$, propyl or isopropyl).

A particularly preferred amine is 3,3'-iminobis(N,N-dimethylpropylamine)

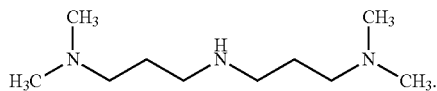

Preferably, the process of the invention as described above can be used for the preparation of the preferred groups of compounds of formula (I) described and defined above, i.e. for compounds of formula (I) wherein $X_1$ and $X_2$ are —$(CH_2)_m$— with m being an integer equal to 2 or from 3 to 20 and $R_1$ to $R_4$ are hydrogen or an alkyl group with 1 to 6 carbon atoms or wherein $X_1$ and $X_2$ are —$(CH_2)_3$— and $R_1$ to $R_4$ are methyl.

The process described above may also be preferably used for the synthesis of compounds of formula (I) wherein $X_1$ and $X_2$ are a branched divalent hydrocarbon group, which may be optionally substituted and/or interrupted by one or more heteroatoms or heteroatom containing groups and $R_1$ to $R_4$ are as defined in claim 1 or wherein $X_1$ and $X_2$ are a branched or linear divalent hydrocarbon group substituted and/or interrupted by one or more heteroatoms or heteroatom containing groups and $R_1$ to $R_4$ are as defined in claim 1.

In accordance with a first preferred embodiment of the process in accordance with the present invention for the preparation of compounds of formula (I) said process comprises a step wherein the internal ketone K1 of formula (III) is synthesized by a process P by decarboxylative ketonization reaction of a fatty acid, a fatty acid derivative or a mixture thereof in a liquid phase with a metal compound as catalyst in a reaction medium, said process P being characterized in that a ketone K2 at liquid state, which is identical or similar to the internal ketone K1, is introduced into the reaction medium.

Suitable metals for use in the process P in the process of the present invention are selected from the group consisting of Mg, Ca, Al, Ga, In, Ge, Sn, Pb, As, Sb, Bi, Cd and transition metals having an atomic number of from 21 to 30. Suitable metal compounds are oxides of the aforementioned metals, carboxylate salts of the aforementioned metals, naphthenate salts of the aforementioned metals or acetate salts of the aforementioned metals, preferably metal compounds are oxides of the aforementioned metals. Magnesium, iron, and their oxides, are particularly preferred as metal compounds.

In accordance with a preferred embodiment the metal compound is iron(II) oxide or iron(III) oxide or a mixed oxide of iron(II) and iron (III) such as e.g. FeO, $Fe_3O_4$ or $Fe_2O_3$. Iron powder has economical advantages as it is cheap and abundantly available. It has been observed that iron oxides are efficient to promote the reaction reducing the overall reaction times.

The catalysis of the reaction may be qualified as a homogeneous catalysis since in the reaction conditions an intermediate metal carboxylate salt (e.g. iron carboxylate) is formed through the initial reaction between the fatty acid or its derivative with the metal compound and this intermediate salt is substantially soluble in the reaction medium.

The process P in accordance with a first embodiment is characterized in that a ketone K2 at liquid state is introduced into a reactor.

The ketone K2 may be identical or similar to the internal ketone K1 to be synthesized.

The ketone K2 has usually a high boiling point, preferably a boiling point of at least 270° C., more preferably at least 290° C., even more preferably at least 310° C. As herein used, the term "boiling point" generally denotes the normal boiling point (also called the atmospheric boiling point or the atmospheric pressure boiling point) of a liquid; it corresponds to the case in which the vapor pressure of the liquid equals the defined atmospheric pressure at sea level, 1 atmosphere. It can be measured by differential scanning calorimetry using for example a METTLER Toledo equipment.

By "a ketone K2 similar to the internal ketone K1", it is to be understood that the difference between the boiling point of the internal ketone K1 and the boiling point of the ketone K2 is equal to or lower than 80° C. Preferably, the difference between the boiling point of the internal ketone K1 and the boiling point of the ketone K2 is equal to or lower than 40° C., preferably equal to or lower than 10° C., more preferably equal to or lower than 5° C., even more preferably equal to or lower than 3° C.

Non limitative examples of ketones suitable as ketone K2 in accordance with process P are 2,2,4,4-tetramethyl-3-pentanone (bp: 152-153° C.), 5-nonanone (bp: 186-187° C.), 8-pentadecanone (bp: 293° C.), heptadecan-8-one (bp: 323° C.), 10-nonadecanone (bp: 35° C.), 12-tricosanone (bp: 404.5° C.), 14-heptacosanone (bp: 454° C.), 16-hentriacontanone (bp: 499.5° C.), 18-pentatriacontanone (bp: 542.5° C.), methyl isobutyl ketone (bp: 117-118° C.), 4-methyl-3-penten-2-one (bp: 130° C.), di isobutyl ketone (bp: 165-170° C.), methyl levulinate (bp: 193-195° C.), trans, trans dibenzylideneacetone (bp: 401° C.), anthraquinone (bp: 379-381° C.), benzophenone (bp: 305° C.), benzoine (bp: 343° C.), acetophenone (bp: 202° C.) and propiophenone (bp: 218° C.).

The ketone K2 is advantageously an internal ketone. The ketone K2 is preferably one or more ketone(s) selected from internal ketones K1 susceptible of being synthesized by the process P, more preferably one or more ketone(s) selected from internal ketones K1 synthesized by the process P. Besides, the ketone K2 introduced into the reaction medium is advantageously one or more ketone(s) selected from ketones having from 7 to 35 carbon atoms, preferably from 15 to 35 carbon atoms. Finally, the ketone K2 introduced into the reaction medium is advantageously one or more ketone(s) selected from aliphatic ketones.

The ketone K2 may consist of one and only one ketone or may be a mixture of ketones. The ketone K2 may a single ketone or a mixture of ketones wherein the ketone(s) is/are susceptible of being obtained by decarboxylative ketonization reaction of a fatty acid, a fatty acid derivative or a mixture thereof. The ketone K2 may be one and only one ketone or a mixture of ketones wherein the ketone(s) has/have been obtained by decarboxylative ketonization reaction of a fatty acid, a fatty acid derivative or a mixture thereof.

When ketone K2 is a mixture of ketones, said mixture may be homogeneous (i.e. uniform in composition) or heterogeneous; it is preferably homogeneous. When ketone K2 is a mixture of ketones, the ketones of which the mixture is composed are generally at least partially miscible with each other; they are preferably fully miscible with each other. When ketone K2 is a mixture of ketones, said mixture of ketones has advantageously one and only one boiling point. In case of a mixture of ketones, the expression "boiling point of the ketone" is to be understood as the boiling point of the mixture of ketones when said mixture of ketones has one and only one boiling point and as the lowest boiling point of the mixture of ketones when said mixture of ketones has several boiling points.

Preferably, the ketone K2 is a mixture of ketones.

According to an embodiment, the ketone K2 introduced originates from a previous process P for synthesizing a ketone by decarboxylative ketonization reaction of a fatty acid, a fatty acid derivative or a mixture thereof, said previous process P being preferably identical to the process P. In such an embodiment, wherein the fatty acid(s)/fatty acid derivatives(s) for producing the ketone K2 is identical to the fatty acid(s)/fatty acid(s) derivative(s) used in step b) of the process P of the invention, the ketone K2 will be very similar or identical to the internal ketone K1.

According to an embodiment of the invention, water formed during the process P is continuously removed from the reaction medium.

According to an embodiment, the reaction medium of process P is substantially free of third solvents.

The term "fatty acid" refers to a carboxylic acid containing at least 4 carbon atoms; besides, a fatty acid contains generally at most 28 carbon atoms. The term "fatty acid derivative" refers to an anhydride made by the condensation of 2 fatty acids or to an ester made by the condensation of a fatty acid with an alcohol.

Suitable fatty acid derivatives are esters and anhydrides of fatty acids, but the use of the free fatty acids as such is generally preferred. The esters or anhydrides in the course of the reaction are converted to the acids which then react with the metal or the metal compound. Especially in case of esters, however, alcohols are formed as a by-product which then has to be removed at a later point in time, which requires additional steps and costs. However, if esters are derived from lower alcohols such as for example methanol, ethanol, propanol or butanol, the alcohols may be removed progressively over the course of the reaction e.g. by reactive distillation.

The fatty acids or fatty acid derivatives can be used in the form of so called fatty acids or fatty acid derivatives cuts which may be obtained by the hydrolysis or alcoholysis of different natural fats and oils. Accordingly these cuts may contain various amounts of different linear fatty acids or linear fatty acid derivatives with different chain lengths. Just by way of examples, fatty acid cuts obtained from coconut oil and comprising mainly $C_{12}$-$C_{18}$ fatty acids may be mentioned here. The skilled person is well aware of other fatty acid cuts obtainable form various sources and will select the best suitable starting materials based on the desired ketones.

According to an embodiment of process P, fatty acids having 12 carbon atoms or less, preferably of from 8 to 12 carbon atoms or derivatives of such acids (esters or anhydrides) constitute at least 10 mol % and preferably at least 15 mol % of the entire molar amount of a fatty acid mixture or fatty acid derivative mixture used as starting material. These acids lead to ketones having a total carbon number of 23 or less which have proved to be advantageous in a number of applications. There is no specific upper limit for the amount of these fatty acids or fatty acid derivatives of acids having 12 carbon atoms or less, i.e. the starting material may also entirely consist of such fatty acids and/or such fatty acid derivatives.

Subject to the above, preferred fatty acids for use in the process P are hexanoic acid, isostearic acid, caprylic acid, capric acid, lauric acid, myristic acid, palmitic acid, stearic acid, arachidic acid, behenic acid, lignoceric acid, cerotic acid or mixtures thereof, and preferred fatty acid derivatives are the esters and anhydrides of these acids.

The fatty acids may be free of any —C=C— double bond of and of any —C≡O— triple bond. Non limitative examples of such fatty acids are the previously cited caprylic acid, capric acid, lauric acid, myristic acid, palmitic acid, stearic acid and mixtures thereof.

Alternatively, the fatty acids may comprise one or more double bonds and/or one or more triple bonds. Examples of fatty acids comprising one or more double bonds are oleic acid, linoleic acid, linolenic acid, erucic acid, palmitoleic acid, ricinoleic acid and mixtures thereof. Examples of fatty acids comprising one or more triple bonds are tariric acid, santalbic acid (which also comprises one double bond) and mixtures thereof.

When starting from a single fatty acid, a single symmetrical ketone is obtained as the reaction product; when starting from a cut of fatty acids as described above all the ketones formed by the combination of the different alkyl groups of the starting acids are obtained and the distribution of the different mixed ketones generally follows a statistical binomial law. The reaction equation can be summarized as follows:

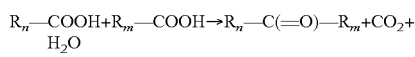

wherein $R_n$ and $R_m$ represent the aliphatic, e.g. alkyl, groups of the fatty acids present in the cut. It is well apparent that e.g. if three different acids are present, a total of six different ketones may be formed; three symmetrical ketones wherein $R_n$ and $R_m$ are identical and three mixed ketones with different groups $R_n$ and $R_m$.

The ketone K1 that is synthetized during the process P is an internal ketone.

According to an embodiment, the total amount of fatty acid material (fatty acid plus fatty acid derivative) added in the reaction medium for the decarboxylative ketonization reaction is such that the overall molar ratio of metal to carboxylic groups is in the range of from 1:6 to 1:99, i.e. the amount of metal is about 1 mol % to about 14 mol % and preferably of from 2 to about 10 mol % of the entire amount of fatty acid and fatty acid derivative.

For most of the processes described in the prior art in the liquid phase the metal or metal compound has been used in amounts of more than 50 mol % and in many cases even exceeding equimolar amounts. Such high amounts of metal are not necessary in the process P in accordance with the present invention which is a technical as well as an economical advantage of the process P over the prior art.

During the decarboxylative ketonization reaction, the temperature of the reaction medium inside the reactor may be maintained at high temperature, for example the temperature inside the reactor may range from 270° C. to 400° C., preferably from 285 to 350° C., more preferably from 300 to 350° C. The reaction medium may be maintained at high temperature until full conversion of fatty acid and disappearance of the optionally formed intermediate metallic salts.

The process P is preferably carried out in an unpressurized system, i.e. without applying superatmospheric pressure. The by-products water and carbon dioxide can be continuously removed during the course of the reaction. Suitable equipment is known to the skilled person and he will use the best suitable equipment set-up for the specific situation. Only by way of example, a so called Dean-Stark trap can be used to remove the water formed during the reaction and such removal represents a preferred embodiment of the present invention.

During the process P, a reaction medium comprising:
at least part of a ketone K2
at least part of the metal compound, and
at least part of the fatty acid, fatty acid derivative or mixture thereof, may be obtained.

According to a particular embodiment the process P comprises the steps of:

S1) introducing at least part of the ketone K2 at liquid state, at least part of the metal compound, at least part of the fatty acid, fatty acid derivative or mixture thereof into a reactor in order to synthesize the internal ketone K1, said reactor optionally containing, before said introduction, a part of the metal compound, a part of the fatty acid, fatty acid derivative or mixture thereof, a part of the ketone K2 and/or a part of the internal ketone K1, S2) recovering the internal ketone K1 together with the ketone K2, S3) optionally recycling at least part of the internal ketone K1 and ketone K2 and/or at least part of the metal compound to the first step S1.

The reaction medium may be formed in the reactor by introducing the different compounds at the first step S1 according to any introduction policy.

According to a preferred embodiment, the metal compound is not mixed with the fatty acid or fatty acid derivative or mixture thereof before introduction into the reactor, in order to avoid the formation of metallic salt outside the reaction medium.

According to an embodiment of the invention, the process P further comprises an additional step after step S1) and before step S2) of maintaining the temperature of the reactor at a high temperature, preferably at a temperature ranging from 270° C. to 400° C., more preferably from 285 to 350°

C., even more preferably from 300 to 350° C., until full conversion of fatty acid and disappearance of the optionally formed intermediate metallic salts.

According to an embodiment, the step S1) of the previous embodiment of the process P of the invention comprises the steps of:

S11) introducing at least part of the ketone K2 at liquid state, and at least part of the metal compound into a reactor, said reactor optionally containing, before said introduction, a part of the metal compound, a part of the fatty acid, fatty acid derivative or mixture thereof, a part of the ketone K2 and/or a part of the internal ketone K1, S12) introducing at least part of the fatty acid, fatty acid derivative or mixture thereof into said reactor, optionally with
- a part of the metal compound and/or
- a part of the intermediate metallic carboxylate salts obtained by reacting metal compound and fatty acid or fatty acid derivative or mixture thereof before decomposition to form the internal ketone K1.

According to an embodiment of the invention, all the ketone K2 may be introduced during step S11) and/or all the fatty acid or fatty acid derivative or mixture thereof may be introduced during step S12).

According to an embodiment wherein the fatty acid, fatty acid derivative or mixture thereof is mixed with the metal compound before introduction into the reaction medium, metallic carboxylate salts may be obtained by a reaction between metal compound and the fatty acid, fatty acid derivative or mixture thereof; said reaction can be carried out at a temperature lower than 270° C.

According to said embodiment, the ketone K2 and the metal compound introduced at step S11) may be introduced separately or together into the reactor. Indeed, the ketone K2 and the metal compound may be mixed outside the reactor, before their introduction into the reactor or the ketone K2 and the metal compound may be mixed into the reactor after their separate introduction into the reactor.

During step S11), at least part of the metal compound is also introduced into the reactor. According to an embodiment, the reactor initially comprises, before step S11), a part of the metal compound, for example, after implementation of step S12) (recovery of the synthetized ketones), a part of the metal compound remains in the reactor. According to another embodiment, all of the metal compound is introduced into the reactor during step S11).

According to an embodiment of process P, at step S11), the reactor is substantially free, in particular totally free, of fatty acid and fatty acid derivative. According to said embodiment, when the ketone K2 is introduced into the reactor, said reactor is substantially free of fatty acid and substantially free of fatty acid derivative.

During step S12), the fatty acid, fatty acid derivative or mixture thereof are introduced in the liquid state into the reactor containing the ketone K2 and the metal compound, for example through a funnel equipping the reactor. They may be added sequentially or continuously and they are profitably added at a rate avoiding the build-up of substantial amounts of free acid in the reaction system as well as significant temperature drop. The progress of the reaction and the conversion of the starting materials to the ketones K1 as final products may be conveniently monitored through appropriate methods like IR analysis.

During step S12), the fatty acid, fatty acid derivative or mixture thereof is generally added over a period of time which depends notably on the overall amount of acid or acid derivative used as well as the overall amount of metal compound present into the reactor.

Once the fatty acid derivative or fatty acid added in the process P of the invention has been converted, the desired internal ketone K1 can be easily recovered e.g. by distillation at reduced pressure. One can take also advantage of the ferromagnetic properties of the at least one metallic compound formed during the reaction (such as iron oxide(s)) to separate the metallic compound from the ketone by applying a magnetic field. Another way to separate the ketone from the metal compound is through a simple decantation or a simple filtration as the metallic compound is not soluble in the reaction mixture containing the ketone obtained as the reaction product. The skilled person is aware of representative techniques so that no further details need to be given here.

At step S2), the internal ketone K1 and the ketone K2 may be recovered together or separately, but preferably together. Indeed, according to a preferred embodiment of the invention, the ketone K2 and the internal ketone K1 are not separated.

The entire process P can be advantageously carried out under inert gas atmosphere and suitable inert gases are e.g. nitrogen or argon, to name only two examples.

The process P can also be done in a continuous way where iron oxides are separated off from the reaction product in another/third separation zone and the residue constituted mainly of iron oxide can be recycled back into the reactor. It has been found, that up to four cycles are possible without a significant loss of catalytic activity of the metal or metal compound.

In another embodiment of the process P, at the end of step S1) the metallic compounds are separated from the products, e.g. using conventional techniques, and then are recycled for the conversion of another batch of fatty acid or fatty acid derivative or mixture thereof preferably comprising at least 10 mol %, based on the entire amount of fatty acid and fatty acid derivative, of fatty acid having 12 carbon atoms or less or derivative of such fatty acid or mixture thereof.

In a same way, part of the ketones recovered at step S2) can be recycled in order to perform step S1) of the process P.

The yield of the desired ketones after step S1) normally exceeds 60%, more preferably 70% and can be as high as more than 90%.

According to an embodiment of the process P of the invention, the reaction medium in the reactor does not contain substantial amount of a third solvent. In a particularly preferred embodiment, no substantial amount of third solvent is added during the process P of the invention. For example, the reactor preferably comprises less than 5% by weight of third solvent(s), more preferably less than 3% by weight of third solvent(s), even more preferably less than 1% by weight of third solvent(s), based on the total weight of the reaction medium, ideally the reactor comprises no third solvent(s).

Within the meaning of the present invention, by the expression "third solvent", it is to be understood, a solvent different from the internal ketone K1, the ketone K2, the fatty acid or fatty acid derivative, the by-products that could be generated during the reaction.

Within the meaning of the present invention, the expression "reaction medium" refers to the medium, within the reactor, wherein the decarboxylative ketonization reaction takes place.

The reactor may be any kind of reactors that are conventionally used for the synthesis of ketones, in particular for the synthesis of ketones in liquid phase.

Within the meaning of the present invention, by "side reactions products", it is to be understood any product formed during the decarboxylative ketonization reaction different from ketones. Among side reaction products, mention may be made of hydrocarbons such as alkanes or alkenes.

The process P may be a continuous or a batch process.

In accordance with another preferred embodiment of the process in accordance with the present invention for the preparation of compounds of formula (I) said process comprises a step wherein the internal ketone K1 of formula (III) is synthesized by a process P for the decarboxylative ketonization of at least one fatty acid, at least one fatty acid derivative or a mixture thereof in a liquid phase with a metal compound as catalyst, characterized in that either a1) in a first step, elementary metal or a metal compound and the fatty acid, fatty acid derivative or mixture thereof comprising at least 10 mol %, based on the entire amount of fatty acid or fatty acid derivative, of fatty acid having 12 carbon atoms or less or derivative of fatty acid having 12 carbon atoms or less, are mixed in a molar ratio of from 1:0.8 to 1:3.5 (molar ratio metal:carboxyl group equivalent) and reacted for a period $P_1$ of from 5 min to 24 h at a temperature $T_1$ of from 100° C. to 270° C. in the substantial absence of added solvent, and b1) thereafter the temperature is raised to a temperature $T_2$ which is strictly above 270° C. and up to 400° C., and additional fatty acid, fatty acid derivative or a mixture thereof comprising at least 10 mol %, based on the entire amount of fatty acid or fatty acid derivative, of fatty acid having 12 carbon atoms or less or derivative of such fatty acid, is added over a period of time $P_2$ of from 5 min to 24 h in the substantial absence of added solvent until the molar ratio of fatty acid, fatty acid derivative or mixture thereof to metal is in the range of from 6:1 to 99:1, or a2) in a first step, elementary metal or a metal compound and the fatty acid, fatty acid derivative or mixture thereof comprising at least 10 mol %, based on the entire amount of fatty acid or fatty acid derivative, of fatty acid having 12 carbon atoms or less or derivative of fatty acid having 12 carbon atoms or less, are mixed in a molar ratio of from 1:0.8 to 1:3.5 (molar ratio metal:carboxyl group equivalent) and reacted for a period $P_1$ of from 5 min to 24 h at a temperature $T_1$ which is strictly above 270° C. and strictly below 300° C. in the substantial absence of added solvent, and b2) thereafter the temperature is raised to a temperature $T_2$ which ranges from 300° C. to 400° C., and additional fatty acid, fatty acid derivative or a mixture thereof comprising at least 10 mol %, based on the entire amount of fatty acid or fatty acid derivative, of fatty acid having 12 carbon atoms or less or derivative of such fatty acid, is added over a period of time $P_2$ of from 5 min to 24 h in the substantial absence of added solvent until the molar ratio of fatty acid, fatty acid derivative or mixture thereof to metal is in the range of from 6:1 to 99:1.

In accordance with the embodiment comprising steps a1) and 131) the following applies:

Temperature $T_1$

Temperature $T_1$ is of from 100° C. to 270° C.

Temperature $T_1$ is preferably of at least 180° C., more preferably of at least 210° C. and still more preferably of at least 230° C.

Besides, temperature $T_1$ may be of at most 260° C.

Temperature $T_1$ may be from 180° C. to 270° C. or from 210° C. to 260° C. Good results were obtained when $T_1$ ranged from 230° C. to 270° C., in particular from 240° C. to 260° C.

Temperature $T_2$

Temperature $T_2$ is strictly above 270° C. and up to 400° C.

Temperature $T_2$ may be strictly below 280° C. However, it is preferably of at least 280° C., more preferably of at least 290° C. and still more preferably of at least 300° C. It may be strictly above 320° C.

Temperature $T_2$ may be strictly above 360° C. However, it is generally of at most 360° C. and often of at most 340° C. It may be of at most 320° C.

Temperature $T_2$ may be from 280° C. to 320° C. Temperature $T_2$ may also be strictly above 320° C. and up to 360° C.

Good results were obtained when $T_2$ ranged from 280° C. to 360° C., in particular from 300° C. to 340° C.

Difference of Temperature $T_2$ Minus $T_1$ ($T_2-T_1$)

Difference of temperature $T_2$ minus $T_1$ is advantageously of at least 3° C. It is preferably of at least 10° C., more preferably of at least 30° C. and still more preferably of at least 45° C.

Besides, $T_2-T_1$ is advantageously of at most 100° C. It may be of at most 85° C., at most 70° C. or at most 55° C.

Good results were obtained when $T_2-T_1$ ranged from 30° C. to 100° C., in particular from 45° C. to 85° C.

Certain Combinations of Temperature $T_1$ and of Temperature $T_2$

In a first embodiment, $T_1$ is from 230° C. to 270° C., while $T_2$ is from 280° C. to 400° C., preferably from 290° C. to 360° C. and more preferably from 300° C. to 340° C.

In a second embodiment, $T_2$ is strictly below 280° C., while $T_1$ is from 180° C. to 270° C., preferably from 230° C. to 270° C. and more preferably from 240° C. to 260° C.

In a third embodiment, $T_2$ is from 280° C. to 320° C., while $T_1$ is from 180° C. to 270° C., preferably from 230° C. to 270° C. and more preferably from 240° C. to 260° C.

In a fourth embodiment, $T_2$ is strictly above 320° C. and up to 360° C., while $T_1$ is from 180° C. to 270° C., preferably from 230° C. to 270° C. and more preferably from 240° C. to 260° C.

In a fifth embodiment, $T_2$ is strictly above 360° C., while $T_1$ is from 180° C. to 270° C., preferably from 230° C. to 270° C. and more preferably from 240° C. to 260° C.

Period of Time $P_1$

Period of time $P_1$ may vary to a large extent depending notably on the nature of the elementary metal or metal compound. In any case, period of time $P_1$ is from 5 min to 24 h.

Period of time $P_1$ is preferably of at least 10 min and more preferably of at least 20 min.

Besides, period of time $P_1$ is preferably of at most 12 h, more preferably of at most 8 h and still more preferably at most 5 h.

Good results were obtained with period of time $P_1$ of from 10 min to 8 h, in particular of from 20 min to 5 h.

Each specified lower limit, upper limit or range for period of time $P_1$ must be considered as explicitly described in combination with each specified lower limit, upper limit or range previously specified for temperature $T_1$.

Period of Time $P_2$

Period of time $P_2$ may also vary to a large extent depending notably on the overall amount of acid or acid derivative used. In any case, period of time $P_2$ is from 5 min to 24 h.

Period of time $P_2$ is preferably of at least 30 min, more preferably of at least 1 h and still more preferably of at least 2 h.

Besides, period of time $P_2$ is preferably of at most 16 h and more preferably of at most 8 h.

Good results were obtained with period of time $P_2$ of from 1 h to 16 h, in particular of from 2 h to 8 h.

Each specified lower limit, upper limit or range for period of time $P_2$ must be considered as explicitly described in combination with each specified lower limit, upper limit or range for temperature $T_2$.

In a certain embodiment of the process P:
temperature $T_1$ is from 180° C. to 270° C., preferably from 210° C. to 260° C.
period of time $P_1$ is from 5 min to 240 min, and
period of time $P_2$ is from 1 h to 24 h.

In accordance with the process P comprising steps a2) and b2) the following applies:

Temperature $T_1$

Temperature $T_1$ is strictly above 270° C. but is strictly below 300° C.

Temperature $T_1$ is preferably at least 275° C., more preferably at least 280° C. and still more preferably least 285° C.

Besides, temperature $T_1$ may be at most 295° C.

Temperature $T_1$ may be from 272° C. to 298° C. or from 275° C. to 295° C. Good results were obtained when $T_1$ ranged from 280° C. to 295° C., in particular from 285° C. to 295° C.

Temperature $T_2$

Temperature $T_2$ is in the range of from 300° C. to 400° C.

Temperature $T_2$ is preferably at least 305° C., more preferably at least 310° C.

Temperature $T_2$ is preferably at most 380° C., more preferably at most 360° C., and often at most 340° C. It may be at most 320° C.

Temperature $T_2$ in a first preferred embodiment E1 (which is exemplified in Example 1) may be of from 320° C. to 360° C., even more preferably from 320° C. to 340° C.

The period $P_2$ is preferably of from 2 to 12 h, still more preferably of from 2 to 8 h.

The molar ratio of metal:carboxylate group equivalent in the first step is preferably in the range of from 1:1.0 to 1:3.0, even more preferably in the range of from 1:1.3 to 1:2.6.

In accordance with another embodiment, temperature $T_2$ is in the range of from 300 to 320° C., preferably in the range of from 305 to 310° C.

In such embodiment period $P_2$ is preferably of from 15 min to 18 h, still more preferably of from 30 min to 17 h and even more preferably of from 1 to 16 h.

Difference of Temperature $T_2$ Minus $T_1$ ($T_2-T_1$)

Difference of temperature $T_2$ minus $T_1$ is advantageously at least 3° C. It is preferably at least 5° C., more preferably at least 15° C.

Besides, $T_2-T_1$ is advantageously at most 100° C. It may be at most 80° C., at most 60° C. or at most 50° C.

Good results were obtained when $T_2-T_1$ ranged from 10° C. to 100° C., in particular from 15° C. to 80° C.

Period of Time $P_1$

Period of time $P_1$ may vary to a large extent depending notably on the nature of the elementary metal or metal compound and the temperature $T_1$. In any case, period of time $P_1$ is from 5 min to 24 h.

Period of time $P_1$ is preferably of at least 10 min and more preferably of at least 20 min.

Besides, period of time $P_1$ is preferably at most 12 h, more preferably at most 8 h and still more preferably at most 6 h.

Good results were obtained with period of time $P_1$ of from 10 min to 8 h, in particular of from 20 min to 6 h.

Each specified lower limit, upper limit or range for period of time $P_1$ must be considered as explicitly described in combination with each specified lower limit, upper limit or range previously specified for temperature $T_1$.

Period of Time $P_2$

Period of time $P_2$ may also vary to a large extent depending notably on the overall amount of acid or acid derivative used and temperature $T_2$. In any case, period of time $P_2$ is from 5 min to 24 h.

Period of time $P_2$ is preferably of at least 15 min, more preferably of at least 1 h and still more preferably of at least 2 h.

Besides, period of time $P_2$ is preferably of at most 18 h and more preferably of at most 16 h.

Good results were obtained with period of time $P_2$ of from 1 h to 18 h, in particular of from 2 h to 15 h.

Each specified lower limit, upper limit or range for period of time $P_2$ must be considered as explicitly described in combination with each specified lower limit, upper limit or range for temperature $T_2$.

The following applies to the process in accordance with the present invention comprising process P with steps a1) and 131) or steps a2) and b2).

In the first step of the process P, elementary metal (or a mixture of elementary metals) or a metal compound (or a mixture of metal compounds) and the fatty acid, fatty acid derivative or mixture thereof comprising at least 10 mol %, based on the entire amount of fatty acid or fatty acid derivatives, of fatty acid having 12 carbon atoms or less or derivative of such fatty acid, are mixed in a molar ratio of from 1:0.8 to 1:3.5 (molar ratio metal:carboxylate group equivalent) and reacted for a period of time $P_1$ at a temperature $T_1$ in the substantial absence of added solvent, preferably in the absence of added solvent.

Suitable metals have been described herein before in connection with the description of the process P comprising the addition of an internal ketone K2 and reference is made thereto to avoid repetitions.

The same applies to the fatty acids and fatty acid derivatives which have also been described hereinbefore for the process P comprising the addition of a ketone K2. Those fatty acids and fatty acid derivatives are also suitable for the process P wherein a1) and 131) respectively a2) and b2) are applied.

It is understood that, when one and only one fatty acid or fatty acid derivative is used as the starting material, it must have 12 carbon atoms or less.

The fatty acids may comprise one or more double bonds in their chains.

Examples of such fatty acids are oleic acid, linoleic acid, linolenic acid, erucic acid, palmitoleic acid and mixtures thereof.

The fatty acids may comprise one or more triple bonds in their chains.

Examples of such fatty acids are tariric acid, santalbic acid and mixtures thereof.

The aliphatic groups of the fatty acids are generally chosen from alkyl, alkenyl, alkanedienyl, alkanetrienyl and alkynyl groups, preferably from alkyl and alkenyl groups, more preferably from alkyl groups.

During the first step of the process P in accordance with the present invention a metal carboxylate is formed as an intermediate species which in the subsequent step decomposes into the desired ketone and a metal oxide which is the active catalytic species for the subsequent conversion of the acid or acid derivative added sequentially or continuously in the second step to the desired ketone containing mixture.

If a metal is used in the first step, said metal reacts with the fatty acid to a carboxylate of the metal with simultaneous formation of hydrogen gas. If a metal oxide is used in the first step, the formation of the carboxylate is accompanied by the simultaneous formation of water. The overall equation for the carboxylate formation in the first step (for a metal having a valency of 2 as example) can be represented as follows:

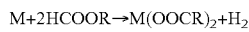

$$M+2HCOOR \rightarrow M(OOCR)_2+H_2$$

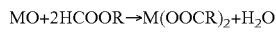

$$MO+2HCOOR \rightarrow M(OOCR)_2+H_2O$$

The molar ratio of metal or metal compound to the total amount of carboxylic groups in the starting material in the first step is in the range of from 1:0.8 to 1:3.5 and it is generally preferred to use a molar ratio which is sufficient to form the respective metal carboxylate and to convert all the acid or acid derivative present to the metal carboxylate, i.e. basically leaving no free carboxylic groups after formation of the carboxylate after the first step. Thus, for a bivalent metal, the molar ratio of metal to carboxylic groups is preferably about 1:2 as two equivalents of acid groups are needed to form the metal dicarboxylate of a bivalent metal. If metal oxide compounds are used instead of elementary metal, the molar ratio referred to above is calculated with the amount of elementary metal in the oxide compound. The molar amount of carboxylic groups is calculated taking into account the number of such groups in the fatty acid or fatty acid derivative which is used as a starting material. Thus, for example an anhydride of an acid comprises two carboxylate functionalities and can provide two carboxylic groups for the formation of the metal carboxylate.

The formation of the metal carboxylate in the first step can be conveniently monitored by in situ IR analysis. The carbonyl absorption band of the acid is subject to a bathochromic shift in the metal carboxylate which allows the monitoring of the reaction progress.

In accordance with a particularly preferred embodiment of the process P, iron powder is used as metal as same is cheap and abundantly available.

Second Step of the Process P

In the second step of the process P comprising steps a1) and 131) respectively a2) and b2), the temperature is raised to temperature $T_2$ at which temperature the metal carboxylate decomposes advantageously to the desired ketone, metal oxide and carbon dioxide.

Additional fatty acid, fatty acid derivative or a mixture thereof comprising at least 10 mol %, based on the entire amount of fatty acid or fatty acid derivative, of fatty acid having 12 carbon atoms or less or derivative of such fatty acid is added in the second step, in the substantial absence of added solvent, preferably in the absence of added solvent. They may be added sequentially or continuously and they are profitably added at a rate avoiding the build-up of substantial amounts of free acid in the reaction system. Again, the progress of the reaction and the conversion of the starting materials to the carboxylates as intermediates and the ketones as final products may be conveniently monitored through appropriate methods like IR analysis.

During the second step, additional fatty acid, fatty acid derivative or a mixture thereof is added over a period of time $P_2$ which depends notably on the overall amount of acid or acid derivative used and the temperature.

For example, in one embodiment, period of time $P_2$ is in the range of from 15 min h to 18 h, preferably of from 1 h to 16 h and particularly preferably of from 2 to 15 hours.

The total amount of fatty acid material (fatty acid or fatty acid derivative) added in the second step of the reaction is such that the overall molar ratio of metal to the amount of carboxylic groups reached at the end of the second step is in the range of from 1:6 to 1:99, i.e. the amount of metal compound is about 1 mol % to about 14 mol % and preferably of from 2 to about 13 mol % of the entire amount of fatty acid or fatty acid derivative, i.e. the metal or metal compound truly functions in a catalytic manner and is not used up in the course of the reaction. For most of the processes described in the prior art in the liquid phase the metal or metal compound has been used in amounts of more than 50 mol % and in many cases even exceeding equimolar amounts. Such high amounts of metal are not necessary in the process P in accordance with the present invention which is a technical as well as an economical advantage of the process P as used herein.

What has been said above for the composition of the starting fatty acid material in the first step of the process P in accordance with the present invention also applies to the second step.

The process P in accordance with the present invention is preferentially carried out in an unpressurized system, i.e. without applying super atmospheric pressure. The by-products water and carbon dioxide can be continuously removed during the course of the reaction. Suitable equipment is known to the skilled person and he will use the best suitable equipment set-up for the specific situation. Only by way of example, a so called Dean-Stark trap can be used to remove the water formed during the reaction and such removal represents a preferred embodiment of the present invention.

The process P can be carried out in the substantial absence of added solvent, preferably in the absence of added solvent. The desired ketone formed during the reaction basically acts as a solvent for the reaction. Since the ketone formed generally as a higher boiling point than the fatty acid, fatty acid derivative or mixture thereof used as starting material, this allows to carry out the reaction in the liquid phase as desired without the addition of an external solvent which would have to be removed at the end of the reaction and which is cost and labour intensive and thus undesirable.

Period of Time $P_{12}$

The additional fatty acid, fatty acid derivative or mixture thereof may be added over period of time $P_2$ under the above specified conditions immediately after the temperature has been raised to $T_2$ (which particular embodiment corresponds to $P_{12}$, as defined hereinafter, equal to 0).

Alternatively, after the temperature has been raised to $T_2$ and before the additional fatty acid, fatty acid derivative or mixture thereof is added over period of time $P_2$, said temperature may be maintained at temperature $T_2$ during a period of time $P_{12}(>0)$.

Period of time $P_{12}$ is preferably at least 30 min and more preferably at least 1 h.

Besides, period of time $P_{12}$ is preferably at most 5 h and more preferably at most 3 h.

Good results were notably obtained with $P_{12}$ ranging from 30 min to 300 min, especially from 1 h to 3 h.

Period of Time $P_{23}$

Immediately after the additional fatty acid, fatty acid derivative or mixture thereof has been added over period of time $P_2$, the temperature may be decreased, possibly down to a temperature $T_3$ which is preferably in the range of from about 5° C. to about 150° C. (which particular embodiment corresponds to P$_{23}$, as defined hereinafter, equal to 0). Temperature T$_3$ may preferably be the room temperature or a temperature slightly above the room temperature.

Alternatively, after the additional fatty acid, fatty acid derivative or mixture thereof has been added over period of time P$_2$, the temperature may be maintained at temperature T$_2$ during a period of time P$_{23}$ (>0).

Period of time P$_{23}$ is preferably at least 30 min and more preferably at least 1 h.

Besides, period of time P$_{23}$ is preferably at most 5 h and more preferably at most 3 h.

Good results were notably obtained when P$_{23}$ ranged from 30 min to 300 min, especially from 1 h to 3 h.

Recovery of the Fatty Acid Ketone and Recycling of Metallic Compounds

The internal ketone synthesized by the process P can be isolated. To this effect, conventional separation means, which are well known to the skilled person, can be used.

Thus, for example, once the fatty acid derivative or fatty acid added in the second step of the process P has been converted, the desired ketone can be easily obtained e.g. by distillation at reduced pressure. One can take also advantage of the ferromagnetic properties of the metallic compounds formed during the reaction (such as iron oxides) to separate the metallic compounds from the ketone by applying a magnetic field. Another way to separate the products ketone from the metal compounds is through a simple filtration as the metallic compounds are not soluble in the ketones obtained as reaction product. The skilled person is aware of representative techniques so that no further details need to be given here.

The entire process P can be advantageously carried out under inert gas atmosphere and suitable inert gases are e.g. nitrogen or argon, to name only two examples.

In accordance with another preferred embodiment, after separation of the desired ketone, the remaining residue constituted mainly of metallic compounds (for example the bottom material after distillation) can be directly reused for a second cycle of addition of fatty acid or fatty acid derivative to be converted to the desired fatty acid ketones. Overall, amounts of as low as one mole percent of metal or metal compound, relative to the amount of carboxylic acid equivalents is sufficient to obtain the desired ketones in good yield. It has been found, that up to four cycles are possible without a significant loss of catalytic activity of the metal or metal compound.

Accordingly, in another preferred embodiment of the process P, at the end of step b1) respectively b2) the metallic compounds are separated from the products using conventional techniques and then are recycled for the conversion of another batch of fatty acid or fatty acid derivative or a mixture thereof comprising at least 10 mol %, based on the entire amount of fatty acid or fatty acid derivative, of fatty acid having 12 carbon atoms or less or derivative of such fatty acid.

The yield of the desired ketones after step two normally exceeds 60 present, more preferably 70% and can be as high as more than 90%.

The compounds of formula (I) can be advantageously used for the preparation of the compounds of formula (II).

Then, in accordance with another process in accordance with the present invention, the compounds of formula (II) are obtained by a process wherein a compound of formula (I) in accordance with the present invention (as defined in claim 1) is reacted with a compound of formula (V) in accordance with the following general scheme

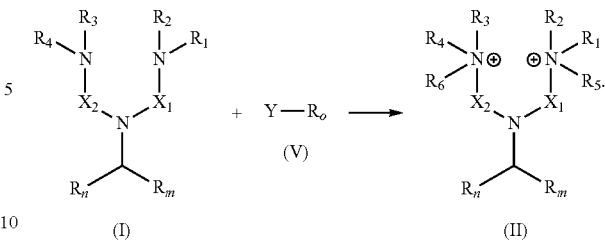

In embodiments wherein the compound of formula (II) is a dibetaine or a disultaine, the compound Y—R$_o$ of formula (V) is such that:

Y is a leaving group; Y is typically a halide such as —Cl, —Br or —I; it can be a sulfonate group such as methanesulfonate (CH$_3$—SO$_3$—), para-toluenesulfonate (C$_7$H$_7$—SO$_3$—) or trifluoromethanesulfonate (CF$_3$—SO$_3$—); Y can be also methylsulfate (—SO$_4$Me) or sulfate (—SO$_4$—); and R$_o$ is -Alk-CH(OH)—CH$_2$—SO$_3$M or -Alk-CO$_2$M, wherein Alk represents an alkylene group (preferably, a C$_1$-C$_{20}$ alkylene group, especially —CH$_2$—) and M is an alkaline metal (typically, Na, K, Li) or hydrogen, preferably an alkaline metal.

From a stoichiometric standpoint, 2 moles of Y—R$_0$ are needed per mole of compound of formula (I) and 2 moles of compound of formula Y-M are formed whenever one mole of compound of formula (II) is formed.

In embodiments wherein the compound of formula (II) is a diaminoxide, Y—R$_o$ (taken as a whole) represents hydrogen peroxide (H$_2$O$_2$).

From a stoichiometric standpoint, two moles of H$_2$O$_2$ are needed per mole of compound of formula (I) and two moles of water (H$_2$O) are formed whenever one mole of compound of formula (II) is formed.

The end compound of formula (II) can be an aminoxide twin-tail amine, that is to say a twin-tail amine substituted by at least one aminoxide containing substituent moiety.

At least one aminoxide twin-tail amine can be obtained from at least one twin-tail tert-amino amine of formula (I) (that is to say a twin-tail amine that is itself substituted by at least one tert-amino group containing substituent), which is itself previously obtained from at least one internal ketone K1.

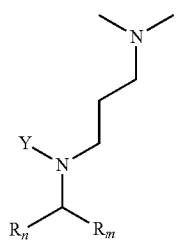

wherein Y in the above formula is a 3-dimethylaminopropyl fragment (—CH$_2$—CH$_2$—CH$_2$—N(CH$_3$)$_2$).

The following reaction scheme can be followed:

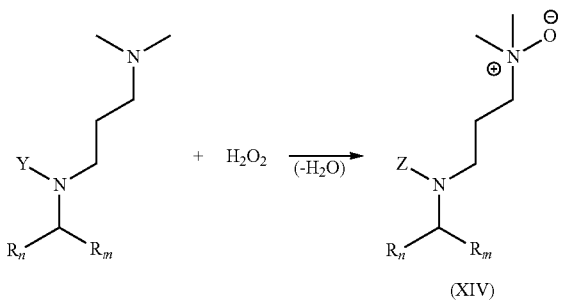

(XIV)

wherein Y in the above formula is a 3-dimethylaminopropyl fragment (—$CH_2$—$CH_2$—$CH_2$—$N(CH_3)_2$) and Z is the 3-dimethylaminoxide propyl fragment (—$CH_2$—$CH_2$—$CH_2$—$N(CH_3)_2O^-$).

This reaction can be conducted by contacting the twin-tail tert-amino amine of formula (I) with $H_2O_2$ (which can be used dissolved in aqueous solution) in a reaction zone at a temperature ranging from 15° C. to 400° C. and optionally in the presence of an added solvent. As examples of suitable solvents, one can mention methanol, ethanol, isopropanol, DMSO, acetonitrile, water, THF, dioxane or a mixture thereof.

In a preferred embodiment, $H_2O_2$ solution is progressively added into the reaction medium and can be used in molar excess with respect of the twin-tail tert-amino amine of formula (I). The excess of $H_2O_2$ can be decomposed at the end of the reaction using appropriate techniques well known by the skilled person of the art.

Making Betaines and Sultaines from Internal Ketones K1 (Compounds of Formula II Wherein $R_o$ is Selected from -Alk-CH(OH)—$CH_2$—$SO_3M$ and -Alk-$CO_2M$)

The end compound of formula (II) can be a dibetaine twin-tail amine, that is to say a twin-tail amine of formula (I) substituted by two betaine moieties, more exactly by two betaine containing substituents.

The end compound of formula (II) can also be a disultaine twin-tail amine, that is to say a twin-tail amine of formula (I) comprising two sultaine moieties, more exactly by tow sultaine containing substituents.

At least one dibetaine twin-tail amine can be obtained from at least one twin-tail di-tert-amino amine (that is to say a twin-tail amine that is itself substituted by two tert-amino groups, more exactly by two tert-amino-containing substituents)—which twin-tail di-tert-amino amine is itself previously obtained from at least one internal ketone K1 that is advantageously synthesized by the process P— by reacting said twin-tail di-tert-amino amine with a compound of formula Y—$R_o$ wherein:

Y is a leaving group, $R_o$ is -Alk-$CO_2M$ with Alk being an alkylene group (in particular, a $C_1$-20 alkylene group) and M being an alkaline metal (typically Na, K, Li) or hydrogen.

Methylene is preferred as the alkylene group Alk.

M is preferably an alkaline metal. Na is preferred as the alkaline metal M.

The leaving group Y is typically a halide such as —Cl, —Br or —I, methylsulfate (—$SO_4Me$), sulfate (—$SO_4$—), a sulfonate derivative such as methanesulfonate (—$O_3S$—$CH_3$), para-toluenesulfonate (—$O_3S$—$C_7H_7$) or trifluoromethanesulfonate (—$O_3S$—$CF_3$).

At least one disultaine twin-tail amine can similarly be obtained from at least one twin-tail di-tert-amino amine which twin-tail di-tert-amino amine is itself previously obtained from at least one internal ketone K1 advantageously synthesized by the process P, by reacting said twin-tail di-tert-amino amine with a compound of formula Y—$R_o$ wherein:

Y is a leaving group, and $R_o$ is Alk-CH(OH)—$CH_2$—$SO_3M$ with Alk being an alkylene group (in particular a $C_1$-$C_{20}$ alkylene group, especially methylene), and M being an alkaline metal (typically Na, K and Li) or hydrogen.

Preferred Y, Alk and M to make the disultaine twin-tail amine are the same as the ones preferred to make the dibetaine twin-tail amine.

To make the dibetaine and/or the disultaine, at least one certain twin-tail amine of formula (I') is advantageously used as reactant:

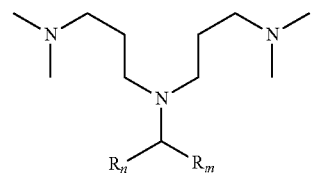

wherein $R_n$ and $R_m$ have the meaning as defined hereinbefore.

Then, at least one dibetaine of formula (IIa) and/or at least one disultaine of formula (IIb) can be prepared from at least one twin-tail amine of formula (I) according to the general scheme:

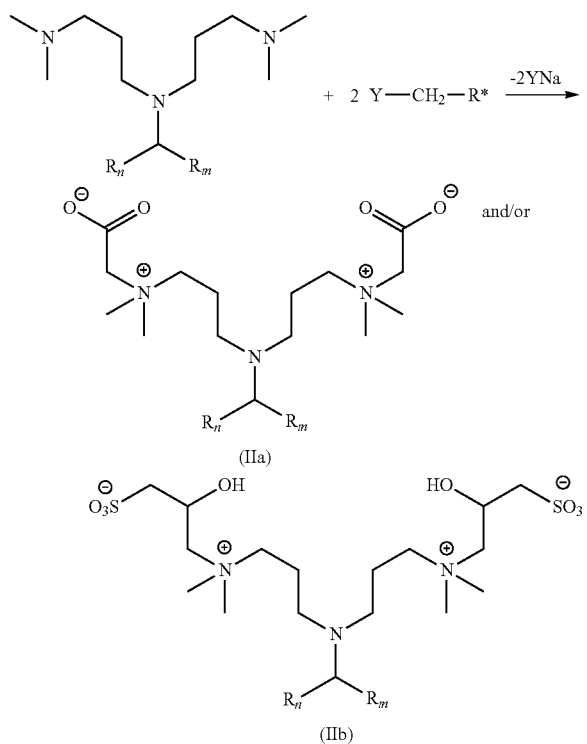

wherein, in the above reaction scheme, Y is the leaving group as previously defined (for example, a halide) and R* is —CO$_2$Na and/or —CH(OH)—CH$_2$—SO$_3$Na.

The above scheme shows the process for each of R$_1$ to R$_4$ being methyl but can be generalized for other meanings of R$_1$ to R$_4$ as defined in claim 1 and the description hereinbefore.

The above scheme shows the process for each Alk (as contained in R$_5$, in R$_6$ and in R$_o$=-Alk-R*) being methylene but can be generalized for other meanings of Alk as defined in claim 1 and the description hereinbefore.

The twin-tail amine (I) is reacted with the alkylating compound Y—CH$_2$—R* to afford the betaine (IIa) or the sultaïne (IIb) depending on the nature of (VI).

Betaïne (IIa) is obtained when R* is —CO$_2$Na and sultaïne (IIb) is obtained when R*=—CH(OH)—CH$_2$—SO$_3$Na. A mixture of betaine and sultaine is obtained when using a mixture of reagents Y—CH$_2$—R* including at least one reagent wherein R* is —CO$_2$Na and at least one reagent wherein R* is —CH(OH)—CH$_2$—SO$_3$Na.

The reaction is usually conducted by contacting the reactants in a reaction zone at temperature from 15° C. to 400° C. and optionally in the presence of an added solvent. As examples of suitable solvents, one can mention methanol, ethanol, isopropanol, DMSO, acetonitrile, water, THF, dioxane and mixtures thereof.

In a preferred embodiment, the pH of the reaction mixture is maintained during the course of the reaction from 8.5 and 9.5. This adjustment can be done by adding required amounts of concentrated NaOH and/or HCl aqueous solutions to the reaction medium during the course of the reaction.

It is a last object of the present invention to provide new valuable compounds, with a particular interest for surfactants.

This last object of the present invention is achieved by a variety of compounds of formula (I) or (II), notably surfactants, susceptible of being prepared by the methods as above described.

The compounds of the present invention have good surfactant properties and are suitable for a large number of different applications, including formulations in the agrochemical area.

The compounds of formula (II) are efficient to reach ultra-low interfacial tension between aqueous solution and acidic crude oils which is of interest for Enhanced Oil Recovery application (surfactant flooding technologies).

Surprisingly, it has been further discovered that the compounds according to the present invention are efficient as drift reduction agents, that is, to (i) reduce the volume weighted proportion of driftable fine particles (diameter<150 μm) and/or (ii) reduce the mean volume diameter of particles enhancing pesticide efficiency.

As used herein, the term "drift" refers to off-target movement of droplets of a pesticide composition that is applied to a target pest or environment for the pest. Spray applied compositions typically exhibit decreasing tendency to drift with decreasing relative amount, typically expressed as a volume percentage of total spray applied droplet volume, of small size spray droplets, that is, spray droplets having a droplet size below a given value, typically, a droplet size of less than 150 micrometers ("μm"). Spray drift of pesticides can have undesirable consequences, such as for example, unintended contact of phytotoxic pesticides with non-pest plants, such as crops or ornamental plants, with damage to such non-pest plants.

Suitable pesticides include, for example, aryloxyphenoxy-propionate herbicides, such as haloxyfop, cyhalofop, and quizalofop, triazine herbicides such as metribuzin, hexaxinone, or atrazine; sulfonylurea herbicides such as chlorsulfuron; uracils such as lenacil, bromacil, or terbacil; urea herbicides such as linuron, diuron, siduron, or neburon; acetanilide herbicides such as alachlor, or metolachlor; thiocarbamate herbicides such as benthiocarb, triallate; oxadiazolone herbicides such as oxadiazon; isoxazolidone herbicides, phenoxy carboxylic acid herbicides such as dichlorophenoxyacetic acid ("2,4-D"), dichlorophenoxybutanoic acid ("2,4-DB"), 2-methyl-4-chlorophenoxyacetic acid ("MCPA"), 4-(4-chloro-2-methylphenoxy)butanoic acid ("MCPB"), dichlorprop, and mecoprop, diphenyl ether herbicides such as fluazifop, acifluorfen, bifenox, or oxyfluorfen; dinitro aniline herbicides such as trifluralin; organophosphonate herbicides such as glufosinate salts and esters and glyphosate salts and esters; dihalobenzonitrile herbicides such as bromoxynil, or ioxynil, benzoic acid herbicides such as dicamba and its salts, dipyridilium herbicides such as paraquat, and pyridine and pyridineoxy carboxylic acid herbicides such as clopyralid, fluroxypyr, picloram, triclopyr, and aminopyralid.

The most common technologies employed for drift reduction are based on the use of high molecular weight soluble polymers. However the use of such polymers has some disadvantages for drift control, which for example include:

(i) that most high molecular weight soluble polymers are in the form of a powder, which is difficult to dissolve and may require additional processing steps or additives;

(ii) that most high molecular weight soluble polymers take a long time to dissolve or disperse, or may result in the unwanted presence of undissolved particles to the end use application, which can clog equipment intended to apply the drift reduction composition; and (iii) that most high molecular weight soluble polymers can undergo mechanical degradation making the solution lose its anti-drift benefits.

Viscoelastic surfactants as low molecular weight soluble drift reduction compounds do not face the above-mentioned drawbacks. In addition, such surfactants can bring additional functionalities such as wetting or improved spreading, which can provide enhancement of pesticide efficiency. The compounds according to the present invention, for example, the bis-zwitterionic surfactants as described herein, are capable of providing drift control benefits, in particular, drift reduction benefits to an aqueous adjuvant or pesticide formulation. A decrease of the proportion of driftable fine particles (diameter<150 μm) and a decrease of the mean volume diameter of particles enhancing pesticide efficiency were observed.

Accordingly, in one aspect described herein are adjuvant composition for modifying the spray properties of an aqueous pesticide composition, comprising the compound of general formula (I) or (II) in an amount that is effective, when the adjuvant composition is diluted in the aqueous pesticide composition and the aqueous pesticide composition is spray applied, to reduce spray drift of the spray applied aqueous pesticide composition compared to an analogous spray applied pesticide composition that lacks the compound of general formula (I) or (II).

In another aspect, described herein are concentrated pesticide compositions, comprising:
a liquid medium,
one or more pesticide compounds, and
the compound of general formula (I) or (II) in an amount that is effective, when the concentrated pesticide composition is diluted and spray applied, to reduce spray drift of the spray applied pesticide composition compared to an analogous spray applied pesticide composition that lacks the compound of general formula (I) or (II).

In a third aspect, described herein are methods for controlling spray drift of an aqueous pesticide composition, comprising:

incorporating in the aqueous pesticide composition the compound of general formula (I) or (II) in an amount that is effective, when the end use pesticide composition is spray applied, to reduce spray drift of the spray applied pesticide composition compared to an analogous spray applied pesticide composition that lacks the compound of general formula (I) or (II), and spray applying the aqueous pesticide composition to a target pest and/or to the environment of the target pest.

Should the disclosure of any patents, patent applications, and publications which are incorporated herein by reference conflict with the description of the present application to the extent that it may render a term unclear, the present description shall take precedence.

The following examples provide further explanations on the present invention.

EXAMPLES

First Set of Examples: Preparation of Internal Ketones from Carboxylic Acids

Example A—Synthesis of 12-Tricosanone Diketone of Lauric Acid

The reaction was carried under argon in a round bottom flask equipped with mechanical stirring, Dean Stark apparatus and an addition funnel. In the reactor, 700 mg of iron powder were dispensed and 20 g of lauric acid was introduced into the addition funnel.

A first partial amount of 5 g of acid was added into the reactor and the temperature was brought to 250° C. The mixture was stirred at this temperature for 30 minutes during which the color of the media changed to black and $H_2$ gas was released.

Then the temperature was raised to 300° C., the mixture was stirred during 1 h 30 and the remaining amount of lauric acid (15 grams) was slowly added into the reactor during 4 h 30 min at a flow rate which allowed keeping concentration of lauric acid in the reaction media very low (no accumulation of free acid in solution).

At the end of the reaction, the addition funnel was replaced by a distillation apparatus and the products were distilled off at 290° C.-340° C. under 5 kPa pressure.

Then the distillation apparatus was replaced by the addition funnel containing a new batch of 20 g of fatty acids and the operations described above were repeated for another cycle. No additional amount of iron was needed. The residue in the flask remaining after distillation was efficient to convert the next batch of acids.

Overall 4 cycles were carried out without any loss of performances reducing thereby the concentration of iron to less than 1 wt % relative to fatty acids amount converted.

The conversion, selectivity and yield (measured by gas chromatography (GC) and isolated) are given in Table 1 below.

TABLE 1

(all values in % of theory)

| Cycle | Conversion | Selectivity | Raw yield | Isolated yield |
|---|---|---|---|---|
| 1 | 100 | 90 | 90 | 77 |
| 2 | 100 | 89 | 89 | 70 |
| 3 | 100 | 87 | 87 | 85 |
| 4 | 100 | 89 | 89 | 87 |

The data show the superior selectivity and yield of the desired ketone.

Example B—Synthesis of C15-C35 Ketones Cut Starting from a C8-C18 Coco Saturated Fatty Acids Cut Using Magnetite (Fe3O4) as the Catalyst 12.5 Mol % of Fe The reaction was carried out under argon in a 750 mL reactor equipped with mechanical stirring, Dean Stark apparatus and an addition funnel. In the reactor, 9.3 g (0.04 mol) of magnetite $Fe_3O_4$ were dispensed and 200 g (0.97 mol) of the coco saturated fatty acids cut (with the following distribution: C8: 7 wt %, C10: 8 wt %, C12: 48 wt %, C14: 17 wt %, C16: 10 wt %, C18: 10 wt %) was introduced into the addition funnel.

A first partial amount of 50 g of fatty acids was added into the reactor and the temperature was brought to $T_1$=290° C. The mixture was stirred at this temperature during 4 hours. During this time the color of the media changed to black and $H_2O$ was formed. FTIR analysis of the crude mixture showed complete formation of intermediate iron carboxylate complexes.

The temperature was then raised to $T_2$=330° C. and the mixture was stirred at this temperature during 2 hours. During this time the intermediate iron carboxylate complexes were decomposed to fatty ketones, iron oxide and $CO_2$. The remaining fatty acids (150 g) are slowly introduced into the reactor such that the temperature of the reaction medium didn't fall down below 320° C. and at a flow rate which allowed keeping concentration of fatty acids in the reaction medium very low (for example with an addition flow rate of around 25 g fatty acids/hour).

Practically this was done through the successive slow additions (1 hour per addition) of 3 portions of 50 g of melted fatty acids with 1 hour of stirring at 330° C. between each addition.

At the end of the last addition, the crude medium is stirred at 330° C. during 2 hours and the reaction progress is monitored through FTIR. When the reaction is completed (no more iron complex detected by FTIR), the mixture is allowed to cool down at room temperature and 400 mL of $CHCl_3$ is added to the crude media. The mixture is stirred at 40° C. in order to solubilize the product. The obtained suspension was filtered on a silica plug (400 g) and eluted using 3 L of chloroform. Evaporation of the solvent afforded 160 g (0.456 mol) of the product $C_{15}$-$C_{35}$ ketones as a white wax (94% isolated yield) analytically pure.

Example C—Ketonization of $C_8$-$C_{18}$ Fatty Acids Cut Using Magnetite Fe3O4 as the Catalyst The reaction is carried out under an inert atmosphere of argon.

In a 750 mL reactor equipped with a mechanical stirrer, a Dean-Stark apparatus to trap water generated during the reaction and an addition funnel, are dispensed 40 g of product $C_{15}$-$C_{35}$ ketones (made through a preliminary ketonization of the starting $C_8$-$C_{18}$ fatty acids) and 9.3 g (0.040 mole) of magnetite $Fe_3O_4$.

The addition funnel of the reactor is filled with 200 g (0.970 mole) of melted fatty acids (C8: 7 wt %, C10: 8 wt %, C12: 48 wt %, C14: 17 wt %, C16: 10 wt %, C18: 10 wt %).

The reaction mixture is then heated at 330° C. under stirring (500 rpm) and 200 g (0.970 mole) of the melted fatty acids is slowly introduced into the reactor such that the temperature of the reaction medium doesn't fall down below 320° C. (for example with an addition flow rate of around 25 g fatty acids/hour).

Practically this can be done also through the successive slow additions (1 hour per addition) of 4 portions of 50 g (60 mL) of melted fatty acids followed by 1 hour of stirring at 330° C. after each addition.

At the end of the last addition, the crude medium is stirred at 330° C. during an additional hour and the reaction progress is monitored through FTIR.

At the end of the reaction when the intermediate iron complex is not detected anymore through FTIR (absorption bands at 1550 cm-1 and 1408 cm-1), the mixture is allowed to cool down at room temperature and dissolved in 400 mL of CHCl3.

The obtained solution is filtered through a path of 400 g of silica gel followed by elution with 5 liters of CHCl3 in order to remove iron oxide.

The chloroform is evaporated under vacuum and the crude product is dried overnight under 10 mbar at 50° C. to obtain 207 g of ketone (which contains 167 g (0.475 mole) of product generated through ketonization of the 200 g of fatty acids in addition to the 40 g of fatty ketones that have been dispensed initially in the reactor) as a light brown wax corresponding to a crude yield of 98%.

Analysis of the crude shows a GC purity of 96% (impurities being mainly hydrocarbons) with the following composition for the ketones cut:

C15: 0.5 wt %, C17: 1.3 wt %, C19: 8.4 wt %, C21: 11.4 wt %, C23: 28.4 wt %, C25: 19.0 wt %, C27: 13.0 wt %, C29: 11.7 wt %, C31: 3.7 wt %, C33: 1.6 wt %, C35: 0.9 wt %.

Second Set of Examples—Synthesis of Twin-Tail Triamines and their Zwitterionic Derivatives Synthesis of Compounds of Formula (I) Using Catalytic Reductive Amination Under $H_2$ Pressure This amination reaction is performed by reacting the ketone (III) and 3,3'-iminobis(N,N-dimethylpropylamine) in the presence of a transition metal (e.g. Ni, Co, Cu, Fe, Rh, Ru, Ir, Pd, Pt) based catalyst (typically Pd/C as one possibility), in an autoclave under hydrogen pressure (typically between 1 atm. and 200 bar).

The reaction can be carried out in a solvent. However, the presence of such a solvent is not compulsory and according to a specific embodiment, no solvent is used for this step. The exact nature of the solvent, if any, may be determined by the skilled person. Typical suitable solvents include, without limitation, water, methanol, ethanol, isopropanol, tert-butanol, THF, 2-methyltetrahydrofuran, 1,4-dioxane, dimethoxyethane, diglyme and mixtures thereof.

This reductive amination is usually carried out at a temperature ranging from 15° C. to 400° C. and may be conducted batch wise, semi-continuously or continuously and generally performed either in a batch mode or in a continuous mode using either a slurry or a fixed bed process (gas-solid or gas-liquid-solid process).

To improve yield and selectivity, generated water can be removed over the course of the reaction thanks for example to a Dean-Stark apparatus using an appropriate solvent such as toluene. Water can also be trapped using for example molecular sieves.

Lewis or Bronsted acidic reactants (for example homogeneous $TiCl_4$, $AlCl_3$, $FeCl_3$, metal triflate compounds, or heterogeneous Amberlyst resins, Aquivion or Nafion Resins, zeolithes, silica-aluminas etc. . . . ) can also be used either in catalytic or stoichiometric amounts to improve yield and kinetics.

Example 1—$C_{23}$ 12-Tricosanone as Starting Material

In a 500 mL round bottom flask equipped with a condenser, a magnetic stirrer, a heater and a temperature probe were added:

10 g of $C_{23}$ ketone, 12-tricosanone (0.030 mole,
13.8 g of 3,3'-iminobis(N,N-dimethylpropylamine) (0.074 mole)
200 mL of dry THF.

The mixture was stirred at room temperature and 16.8 g of $T_i(OiPr)_4$ (0.059 mole) was added into the mixture.

The mixture was then allowed to cool down at room temperature and 100 mL of methanol was added followed by the careful addition of 1.1 g of $NaBH_4$ (0.030 mole). During $NaBH_4$ addition, gas generation was observed causing some foaming.

The mixture was then stirred at room temperature during 4 h and 200 mL of water was then added causing precipitation of $TiO_2$.

200 mL of ether was then added into the reaction vessel and the suspension was filtered. The biphasic filtrate was then decanted and the organic phase was washed 3 times using a NaOH (0.5 M) aqueous solution. The organic phase was finally dried over $MgSO_4$, filtered and evaporated to give yellow oil.

The crude product was then purified by flash chromatography with an automated Combiflash apparatus using an eluent going from 100% $CH_2Cl_2$ (containing 1 wt % of $NEt_3$) to a mixture of $CH_2Cl_2$:MeOH (80:20 containing 1 wt % of $NEt_3$).

After collection of fractions and solvent evaporation, 4.7 g (0.009 mole) of pure product is obtained as a colorless oil corresponding to a yield of 32%.

Example 2—from $C_{27}$ Heptacosan-14-One

In a 2 liters double jacketed reactor equipped with a mechanical stirrer (propeller with four inclined plows), a temperature probe and a condenser were added:

160 g of $C_{27}$ ketone (0.405 mole)
190 g of 3,3'-iminobis(N,N-dimethylpropylamine) (1.014 moles)
500 mL of dry THF.

The mixture was stirred at room temperature and 230 g of $T_i(OiPr)_4$ (0.809 mole) was added into the reactor.

The mixture was then stirred at 65° C. (THF reflux) during 24 hours (it was observed that at this temperature the mixture became transparent→no suspension anymore).

The reaction mixture was then allowed to cool down to room temperature and 400 mL of methanol were added.

Then 15.33 g of $NaBH_4$ (0.405 mole) was progressively added into the mixture. During $NaBH_4$ addition, gas release was observed.

The mixture was then stirred at room temperature during 4 hours.

300 mL of water was then added (precipitation of $TiO_2$ was observed) followed by 500 mL of diethyl ether.

The suspension was filtered in order to remove $TiO_2$ and the filtrate was decanted in order to separate organic phase and aqueous phase.

The organic phase obtained from filtrate was then washed 3 times with an aqueous NaOH [0.5M] solution, dried over $MgSO_4$, filtered and evaporated to afford 137 g of orange oil.

The oil was then purified by flash chromatography with automated Combiflash apparatus using an eluent going from 100% $CHCl_3$ (containing 3 wt % of $NEt_3$) to a mixture of $CHCl_3$:MeOH (75:25 containing 3 wt % of $NEt_3$).

4 clean fractions were collected and evaporated affording 82 g of oil (0.145 mole) of analytically pure compound (36% isolated yield, 43% selectivity when considering the unreacted ketone which has been recovered, 84% of ketone conversion).

Example 3—Twin Tail Triamine from $C_{31}$ Hentriacontan-16-One

In a 2 L double-jacketed reactor equipped with a mechanical stirrer (propeller with four inclined plows), a condenser and a temperature probe were added:
  25.3 g of hentriacontan-16-one (0.056 mole)
  26.1 g of 3,3'-iminobis(N,N-dimethylpropylamine) (0.139 mole)
  200 mL of dry THF.

The mixture was stirred at room temperature and 31.6 g of $T_1(OiPr)_4$ (0.111 mole) were added into the mixture. The mixture was then stirred at 65° C. (THF reflux) during 3 days. After cooling down to room temperature, 80 mL of dry methanol was added into the reactor vessel followed by the progressive addition of $NaBH_4$ (2.2 g, 0.057 mole) (foaming occurring during $NaBH_4$ addition).

The mixture was then stirred at room temperature during 4 hours and 200 mL of ether followed by 200 mL of water were added. During water addition $TiO_2$ precipitated as a white solid.

The mixture was filtered and the biphasic filtrate was decanted in order to recover the organic phase. The aqueous phase was extracted 3 times with 200 mL of ether, the organic fractions are collected and then washed 3 times with 200 mL of an aqueous NaOH solution (0.5 M).

The organic phase was dried over $MgSO_4$, filtered and evaporated to afford orange oil.

As the $TiO_2$ solid filtered previously could have contained additional amounts of products, it was washed with 200 mL of ether followed by 500 mL of 80/20 mixture of $CHCl_3$/MeOH containing 2 wt % of $NEt_3$.

The obtained organic phase was then washed three times with 300 mL of an aqueous NaOH solution (0.5 M), dried over $MgSO_4$, filtered and evaporated. The obtained oil was combined with the previously recovered oil.

The crude oil was then purified by flash chromatography with automated Combiflash apparatus using an eluent going from 100% $CHCl_3$ (containing 2 wt % of $NEt_3$) to a mixture of $CHCl_3$:MeOH (75:25 containing 2 wt % of $NEt_3$).

6.44 g of the starting ketone containing 10 mol % of alcohol was recovered along with 11.12 g (0.018 mole) of the purified triamine corresponding to 32% isolated yield, 42% selectivity when considering the unreacted ketone which has been recovered, 77% of ketone conversion.

Example 4—Synthesis of Betaines—from $C_{27}$ Triamine

In a 500 mL round bottom flask equipped with a magnetic stirrer, a heater, a condenser, a temperature probe and pH-meter were added:
  43.7 g of the $C_{27}$-triamine (0.077 mole)
  41 mL of water
  35 mL of isopropanol.

The mixture was stirred at room temperature and 18.9 g of sodium monochloroacetate (0.162 mole) was added. The reaction medium was then stirred at 90° C. (oil bath temperature) and the pH of the mixture was continuously monitored.

During the reaction the pH was kept around 9+/−0.5. Once the pH decreased below 8.5, drops of concentrated NaOH aqueous solution (12M) were added progressively to maintain pH around 9.

The reaction progress was monitored using $^1H$ NMR.

Stirring at 90° C. was kept until triamine conversion was >99%.

If necessary, additional amount of sodium monochloroacetate (+0.05 equivalent) can be added into the mixture to achieve triamine conversion to the extent desired.

At the end of the reaction, the mixture was cooled down to room temperature and the desired betaine was obtained as a 40 wt % homogeneous solution that could be used as such.

Example 5—Betaines Form $C_{23}$ or $C_{31}$ Triamine

The same protocol as described in Example 4 was used to obtain the respective betaines with similar results and yields.

Example 6—Synthesis of Amine-Oxides from $C_{27}$ Triamine

In a 100 mL round bottom flask equipped with a magnetic stirrer, a condenser, a heater, a temperature probe and a syringe containing 8 g of $H_2O_2$ (30%) (0.071 mole) were added:
  10 g of the triamine $C_{27}$ (0.018 mole)
  2.6 mL of water
  8.1 mL of isopropanol.

The mixture was then stirred at 75° C. and the $H_2O_2$ aqueous solution was progressively added over a period of time of 2 h.

One could observe that the reaction became monophasic upon $H_2O_2$ addition.

The reaction progress was followed using $^1H$ NMR and after 1 h of stirring at 75° C. after the end of $H_2O_2$ addition, the mixture was cooled down to 50° C. and 0.1 g of Pd/C (3%) were added. The mixture was stirred at 50° C. overnight in order to dismute excess of $H_2O_2$.

The mixture was cooled down to room temperature and filtered.

The filtrate was evaporated and lyophilized to afford a solid residue which was then purified by a filtration over silica.

The eluent used was a $CHCl_3$:MeOH solvent mixture (containing 2 wt % of $NEt_3$) with a gradient going from 100:0 ($CHCl_3$:MeOH) to 0:100 ($CHCl_3$:MeOH).

After fractions collection and solvent recuperation, 6.6 g (0.011 mole) of a yellow oil analytically pure was recovered corresponding to a yield of 62%.

Example 7—Amine Oxides Form $C_{23}$ or $C_{31}$ Triamine

The respective amine oxides could be obtained in similar yields using the protocol of Example 6.

Example 8—Surfactant Properties of Betaines

Solubility and phase behavior of mixtures of 027 and 031 di-betaine surfactants were tested in presence of crude oils. It is known that betaine interacts with polar components present in acid crude oils (Total Acid Number (TAN)>0.7 mg NaOH/g crude oil), for reaching low interfacial tension between the water and the oil.

Di-betaines soluble in water showed the same behavior when mixtures of $C_{27}$ and $C_{31}$ were put in contact with an acid crude oil (TAN=2). In FIG. 1, dynamic Interfacial tension of this acid oil in presence of di-betaines mixtures is shown. As could be observed, for a mixture of 28% mol of $C_{31}$ in a binary mixture with $C_{27}$, a minimal value for interfacial tension (IFT) of around $1*10^{-4}$ mN/m was reached. This value is lower than the IFT reached with linear betaines ($C_{16}$-$C_{18}$) under the same conditions ($1*10^{-2}$ mN/m). This property of di-betaines means that interactions with crude oil are stronger than for than linear betaines, making the di-betaines more efficient than linear betaines for enhanced oil recovery (EOR) application.

The new compounds in accordance with the present invention molecules could be used for reaching low interfacial tensions with crude oils with a limit of TAN of 0.8 mg NaOH/g crude oil.

Example 9—Di-Betaine Surfactants for Drift Reduction

Figure 2:
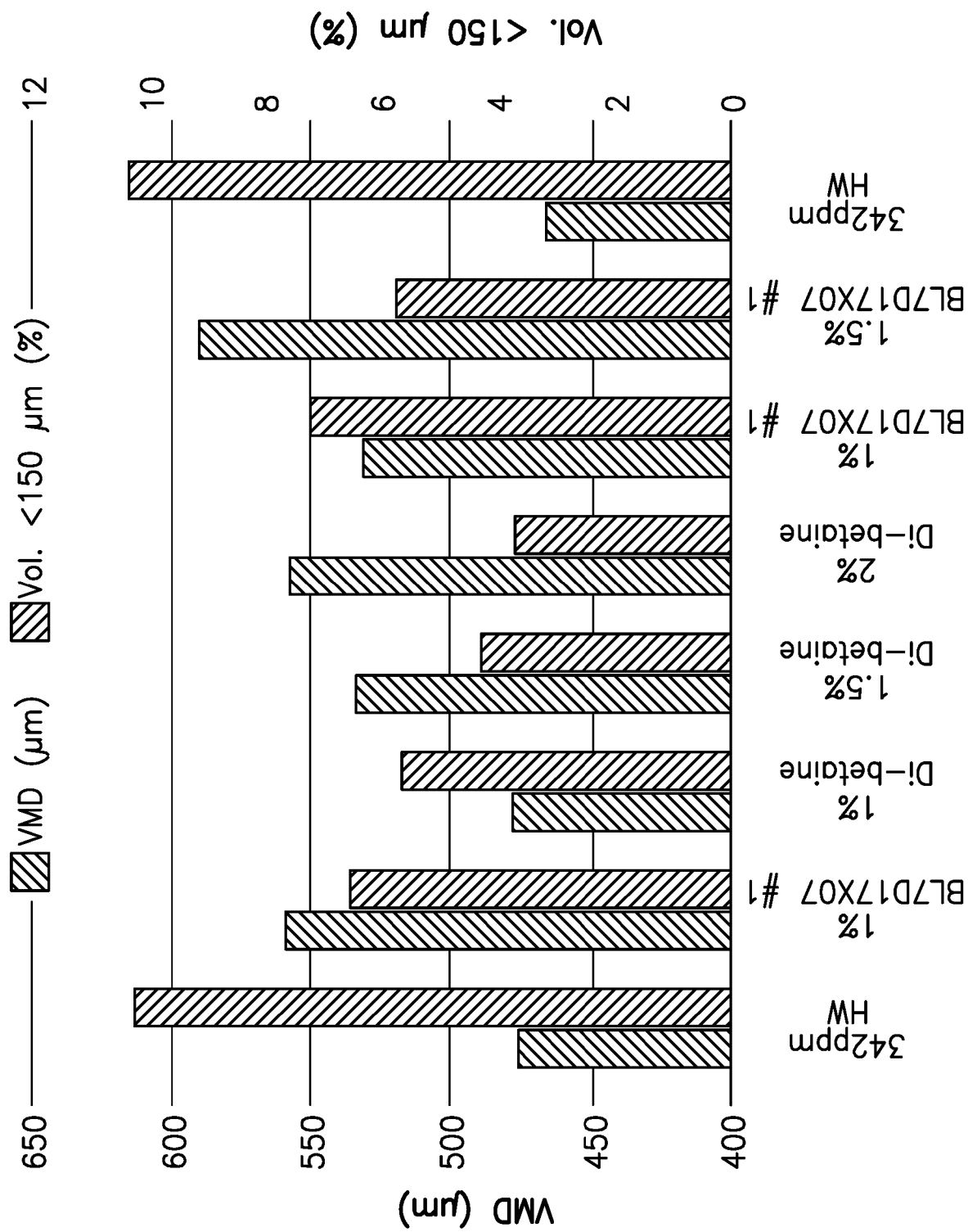
FIG. 2 shows driftable fines [Vol<150 μm (%)] and average particle size distribution [VMD(μm)] of different concentrations (1%, 1.5% and 2%) of dibetaine $C_{31}$ as compared to a commercially available drift control product (1% and 1.5% commercial product—BL7D17X07 #1) and control.
Figure 3:
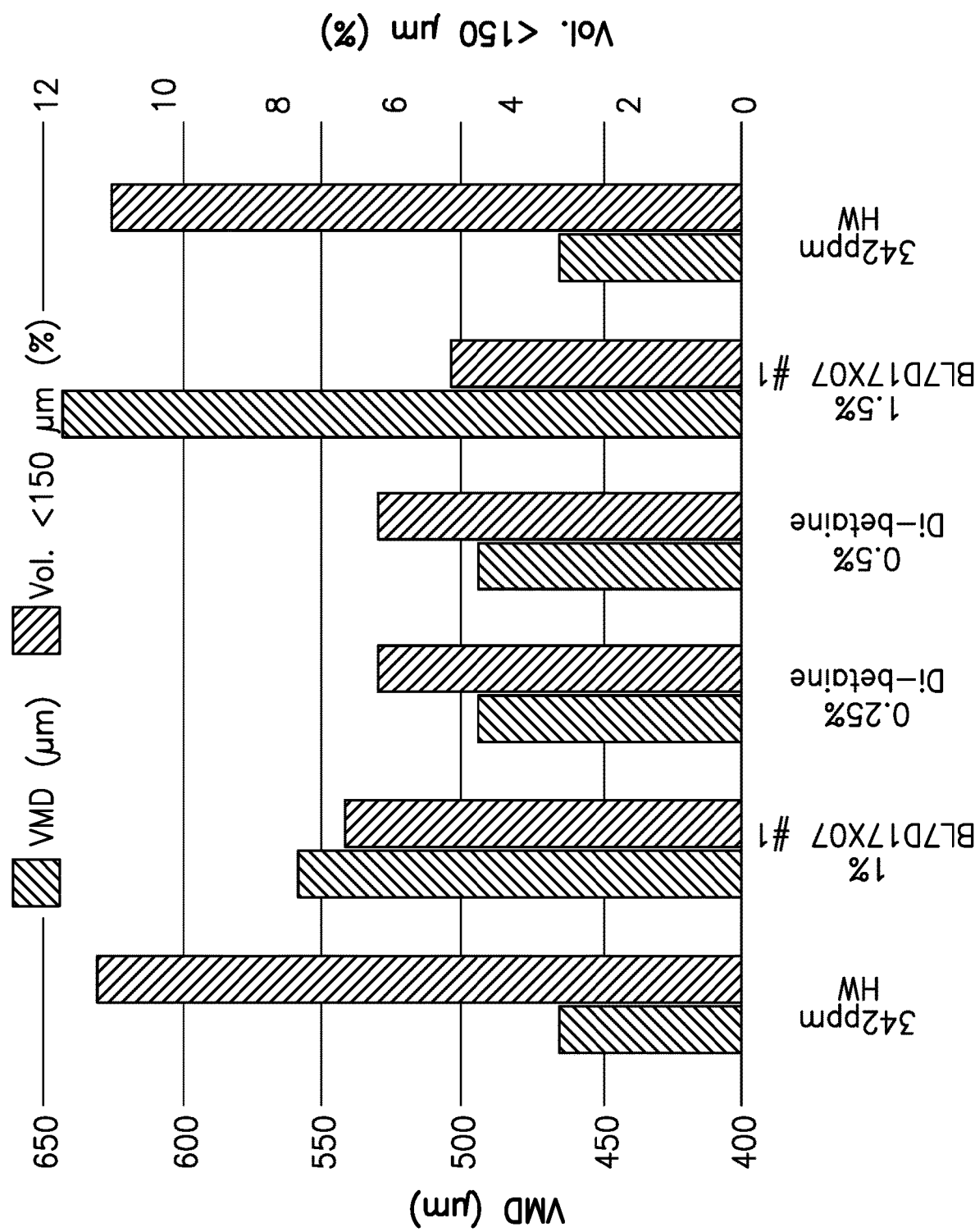
FIG. 3 shows driftable fines [Vol<150 μm (%)] and average particle size distribution [VMD(μm)] of different concentrations (0.25% and 0.5%) of dibetaine $C_{31}$ as compared to a commercially available drift control product (1% and 1.5% commercial product—BL7D17X07 #1) and control.

IKD Dibetaine C31 as a solution in a (60:40) water: isopropanol mixture at 37 wt % concentration was investigated for drift reduction properties. 0.25%, 0.5%, 1%, 1.5% and 2% concentration of solution IKD Dibetaine C31 were prepared in 342 ppm water and mixed for 10 min. (The term "IKD", as used herein, means that the dibetaine was obtained from at least one internal ketone, i.e., through internal ketone functionalization or internal ketone derivation.) Mixing was carried out using magnetic stirrer with the speed adjusted to create vortex. AI11003-VS was used for the test on Sympatec HELOS laser spray at 40 psi pressure. Referring to FIGS. 2 and 3, different concentrations (0.25% 0.5%, 1%, 1.5% and 2%) of solution IKD dibetaine 031 showed a reduction in driftable fines and a reduction in average particle size distribution when it was compared to a commercially available drift control product (1% and 1.5% commercial product—BL7D17X07 #1) and control (342 ppm HW).

The invention claimed is:

1. A compound of general formula (II)

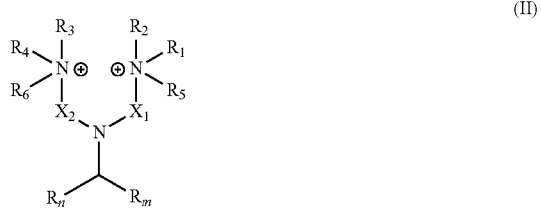

(II)

wherein $R_n$ and $R_m$ are independently selected from the group consisting of $C_3$-$C_{27}$ alkyl and $C_3$-$C_{27}$ alkenyl groups, $X_1$ and $X_2$ are —$(CH_2)_3$— and $R_1$ to $R_4$ are methyl, and $R_5$ and $R_6$, which may be the same or different at each occurrence, represent a group selected from —$O^-$, -Alk-CH(OH)—$CH_2$—$SO_3$— and -Alk-$CO_2$— wherein Alk represents a methylene group —$CH_2$—.

2. The compound in accordance with claim 1 wherein the compound is a compound of general formula (II) in which $X_1$ and $X_2$ are —$(CH_2)_3$—, $R_1$ to $R_4$ are methyl and $R_5$ and $R_6$ are —$CH_2$—CH(OH)—$CH_2$—$SO_3$— or —$CH_2$—$CO_2$—.

3. The compound in accordance with claim 1 wherein the compound is a compound of general formula (II) in which $X_1$ and $X_2$ are —$(CH_2)_3$—, $R_1$ to $R_4$ are methyl and $R_5$ and $R_6$ are —$O^-$.

4. A process for the preparation of a compound according to claim 1, wherein the compound is a compound of formula (II), the process comprising reacting a compound of formula (I) with a compound of formula (V) in accordance with the following general scheme

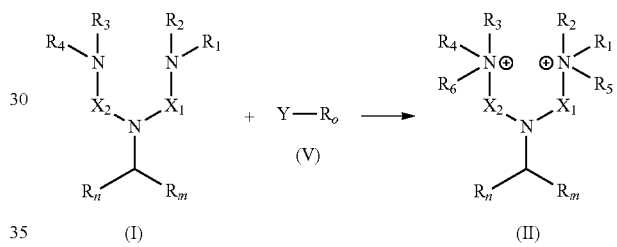

wherein $R_n$ and $R_m$ are independently selected from the group consisting of $C_3$-$C_{27}$ alkyl and $C_3$-$C_{27}$ alkenyl groups, $X_1$ and $X_2$ are —$(CH_2)_3$— and $R_1$ to $R_4$ are methyl, and wherein Y—$R_0$ represents either hydrogen peroxide or a compound in which Y is a leaving group and $R_0$ is -Alk-CH(OH)—$CH_2$—$SO_3$M or -Alk-$CO_2$M, wherein Alk represents a methylene group —$CH_2$— and M is an alkaline metal or hydrogen.

5. The process of claim 4 wherein Y—$R_0$ represents a compound in which Y is a leaving group and $R_0$ is -Alk-CH(OH)—$CH_2$—$SO_3$M or -Alk-$CO_2$M.

6. The process of claim 5 wherein M is an alkaline metal.

7. The process of claim 5 wherein $R_0$ is —$CH_2$—CH(OH)—$CH_2$—$SO_3$Na or —$CH_2$—$CO_2$Na.

8. The process of claim 4 wherein the compound of formula (I) is reacted with hydrogen peroxide in a reaction zone at a temperature ranging from 15 to 400° C. and optionally in the presence of an added solvent.

9. The process of claim 4, additionally comprising preparing the compound of formula (I) by a process comprising reacting an internal ketone K1 of formula (III) with a twin-tail amine of formula (IV) under reductive amination conditions in accordance with the following general reaction scheme.

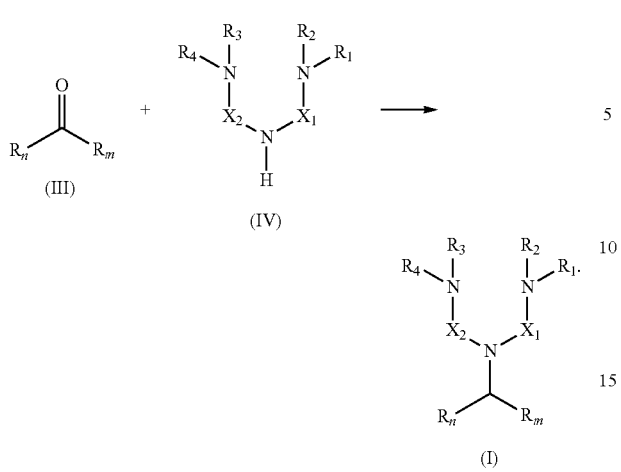

(III) (IV) (I)

10. A method, comprising using a compound according to claim 1, wherein the compound is a compound of formula (II), for enhanced oil recovery application.

11. An adjuvant composition for modifying the spray properties of an aqueous pesticide composition comprising:

a compound of general formula (II)

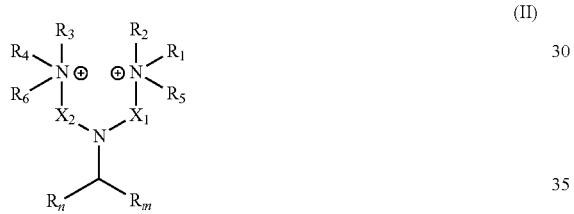

(II)

wherein $R_n$ and $R_m$ are independently selected from the group consisting of $C_3$-$C_{27}$ alkyl and $C_3$-$C_{27}$ alkenyl groups, $X_1$ and $X_2$ are $-(CH_2)_3-$ and $R_1$ to $R_4$ are methyl, and $R_5$ and $R_6$, which may be the same or different at each occurrence, represent a group selected from $-O^-$, -Alk-CH(OH)—$CH_2$—$SO_3$— and -Alk-$CO_2$—, wherein Alk represents a methylene group $-CH_2-$, in an amount that is effective, when the adjuvant composition is diluted in the aqueous pesticide composition and the aqueous pesticide composition is spray applied, to reduce spray drift of the spray applied aqueous pesticide composition compared to an analogous spray applied pesticide composition that lacks the compound of general formula (II).

12. A method for controlling spray drift of an aqueous pesticide composition, comprising:

incorporating in the aqueous pesticide composition a compound of general formula (II)

(II)

wherein $R_n$ and $R_m$ are independently selected from the group consisting of $C_3$-$C_{27}$ alkyl and $C_3$-$C_{27}$ alkenyl groups, $X_1$ and $X_2$ are $-(CH_2)_3-$ and $R_1$ to $R_4$ are methyl, and $R_5$ and $R_6$, which may be the same or different at each occurrence, represent a group selected from $-O^-$, -Alk-CH(OH)—$CH_2$—$SO_3$— and -Alk-$CO_2$—, wherein Alk represents a methylene group $-CH_2-$, in an amount that is effective, when the end use pesticide composition is spray applied, to reduce spray drift of the spray applied pesticide composition compared to an analogous spray applied pesticide composition that lacks the compound of general formula (II), and spray applying the aqueous pesticide composition to a target pest or to an environment of the target pest.

13. A method, comprising using the compound of formula (II) prepared by the process according to claim 4 for an enhanced oil recovery application.

14. The compound in accordance with claim 1, wherein $R_n$ and $R_m$ are independently $C_3$-$C_{27}$ alkyl groups.

* * * * *

UNITED STATES PATENT AND TRADEMARK OFFICE
CERTIFICATE OF CORRECTION

PATENT NO. : 11,186,538 B2
APPLICATION NO. : 16/347994
DATED : November 30, 2021
INVENTOR(S) : Back et al.

It is certified that error appears in the above-identified patent and that said Letters Patent is hereby corrected as shown below:

In the Claims

At Column 32, Claim number 1, Line number 7, "–Alk–CH(OH)–CH$_2$–SO$_3$–" should read -- –Alk–CH(OH)–CH$_2$–SO$_3^-$ --, and "–Alk–CO$_2$–" should read -- –Alk–CO$_2^-$ --.

At Column 32, Claim number 2, Line numbers 13-14, "–CH$_2$–CH(OH)–CH$_2$–SO$_3$–" should read -- –CH$_2$–CH(OH)–CH$_2$–SO$_3^-$ --, and "–CH$_2$–CO$_2$–" should read -- –CH$_2$–CO$_2^-$ --.

At Column 33, Claim number 11, Line number 44, "–Alk–CH(OH)–CH$_2$–SO$_3$–" should read -- –Alk-CH(OH)–CH$_2$–SO$_3^-$ --, and "–Alk–CO$_2$–" should read -- –Alk–CO$_2^-$ --.

At Column 34, Claim number 12, Line number 30, "–Alk–CH(OH)–CH2–SO$_3$–" should read -- –Alk-CH(OH)–CH$_2$–SO$_3^-$ --, and "–Alk–CO$_2$–" should read -- –Alk–CO$_2^-$ --.

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*